United States Patent
Atkinson et al.

(10) Patent No.: US 6,680,424 B2
(45) Date of Patent: *Jan. 20, 2004

(54) MODIFIED PROTEINASE INHIBITORS

(75) Inventors: Howard John Atkinson, Near Settle (GB); Michael John McPherson, Thornhill (GB); Peter Edward Urwin, Bramley (GB)

(73) Assignee: University of Leeds, Leeds (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/849,303

(22) PCT Filed: Nov. 20, 1995

(86) PCT No.: PCT/GB95/02711

§ 371 (c)(1),
(2), (4) Date: May 21, 1997

(87) PCT Pub. No.: WO96/16173

PCT Pub. Date: May 30, 1996

(65) Prior Publication Data

US 2003/0221209 A1 Nov. 27, 2003

(30) Foreign Application Priority Data

Nov. 21, 1994 (GB) .............................. 9423450
Nov. 21, 1994 (GB) .............................. 9423477

(51) Int. Cl.[7] .................. C12N 15/09; C12N 15/29; C12N 15/82; A01H 5/00
(52) U.S. Cl. .................. 800/279; 800/278; 800/298; 435/69.1; 435/69.2; 435/419; 435/468; 435/320.1; 435/410; 536/23.6; 536/24.1; 530/370
(58) Field of Search .................. 536/23.6, 24.1; 435/69.1, 468, 419, 410, 320.1, 69.2; 800/278, 279, 298; 530/370

(56) References Cited

U.S. PATENT DOCUMENTS 5,124,443 A 6/1992 Colella et al.

FOREIGN PATENT DOCUMENTS

| EP | 348348 | 12/1989 |
|---|---|---|
| EP | 502730 | 9/1992 |
| EP | 511393 | 11/1992 |
| GB | 94/038197 | 11/1994 |
| WO | WO 88/09384 | 12/1988 |
| WO | WO 92/0611 | 4/1992 |
| WO | WO 93/04082 | 3/1993 |
| WO | WO 95/23229 | 8/1995 |

OTHER PUBLICATIONS

Boase et al. 1998. In Vitro Cellular and Developmental Biology. 1998. vol. 34: 46–51.*
Linthorst et al. Plant Cell. 1989. vol. 3: 285–291.*
Masoud et al. Plant Molecular Biology. 1993. vol. 21: 655–663.*
Arai et al. J. Biochem. 1991. vol. 109: 294–298.*
Spencer et al. 1992. vol. 12: 201–210.*

(List continued on next page.)

*Primary Examiner*—Elizabeth F. McElwain
*Assistant Examiner*—Medina A. Ibrahim
(74) *Attorney, Agent, or Firm*—Klauber & Jackson

(57) ABSTRACT

The invention relates to proteinase inhibitors and in particular cystatins which have been modified so as to enhance the effectiveness of synthetically manufactured counterparts. The modifications include either site-directed alterations in the structure of the protein and/or the production of hybrid molecules.

15 Claims, 7 Drawing Sheets

OTHER PUBLICATIONS

Lazar et al. "Transforming Growth Factor x: Mutation of Aspartic Acid 47 and Leucine 48 Results in Different Biological Activities", Mar. 1988, Molecular and Cellular Biology, vol. 8, No. 3, pp. 1247–1252.*

Broun et al, "Catalytic Plasticity of Fatty Acid Modification Enzymes Underlying Chemical Diversity of Plant Lipids", Nov. 1998, Science vol. 282, pp.. 1315–1317.*

Chen MS et al.(1992) Protein Expression Purif 3:41–49.
Stubbs et al. (1990) EMBO Journal 9:1939–1947.
Ray C.et al. (1992) Mole & Biochemi. Parasi. 51:239–250.
Fernandes et al.(1993)Plant Mol. Biol. 23:215–219.
Masouds S A et al.(1993)Plant Mol. Biol. 21:655–663.
Urwim P E et al.(1995)Plant Jounal 8:121–131.

* cited by examiner

FIG. 1A

```
              1:::::::::11:::::::::21:::::::::31:::::::::41:::::::::51:::::::::61:::::::::71:::
CYTA_HUMAN    ------------------------------------------------------------MIPGGL----SEAKPATPEIQEIVDK
CYTA_RAT      ------------------------------------------------------MDPGTTGIVGGV----SEAKPATPEIQEVADK
CYTB_RAT      --------------------------------------------------------MMCGAP----SATMPATTETQEIADK
CYTB_BOVIN    --------------------------------------------------------MMCGGT----SATQPATAETQAIADK
CYT1_MOUSE    ----------------------------------------------------MSQENLKIKGGL----SEARPATPEIQMIADK
CYT2_MOUSE    ----------------------------------------------------MTEYTIEIIGGL----SEARPATSEIQEIADK
CYT3_MOUSE    --------------------------------------------------------MSLGGV----SEASRATPEIQMIANK
CYTB_HUMAN    --------------------------------------------------------MMCGAP----SATQPATAETQHIADQ
CYT1_ORYZA    ------------------------------------------------MSSDGGPVLGGV----EPVGNENDLHLVDLARF
CYT1_ORYZA-D86 ------------------------------------------------MSSDGGPVLGGV----EPVGNENDLHLVDLARF
CYT2_ORYZA    ---------------------------MAEEAQSHAREGGRHPRQPAGRENDLTTVELARF
CYT_COWP      --------------------------------------------------MAALGGN-RDVAGNQNSLEIDSLARF
CYT1_MAIZE    ------------MRKHRIVSLVAALLVLLALAAVSSTRSTQKESVADNAGMLAGGI-KDVPANENDLQLQELARF
CYT2_MAIZE    ------------MRLHRIVSLVAALLILLALAVSSTRNAQEDSMADNTGTLAGGI-KDVPGNENDLHLQELARF
CYT_CHICK     ----------------MAGARGCVVLLAAALMIVGAVLGSEDRSRLLGAP---VPVDENDEGLQRALQF
CYTC_BOVIN    -----------------------------------------RLLGGL---MEADVNEEGVQEALSF
CYTC_HUMAN    -------MAGPLRAPLLLLAILAVALAVSPAAGSSPGKPPRLVGGP----MDASVEEEGVRRALDF
CYTC_MOUSE    -------MASPLRSLLFLLAVLGVAWAATPKQGPRMLGAP----EEADANEEGVRRALDF
CYTC_RAT      -----------------VLAVAWAGTSRPPPRLLGAP----QEADASEEGVQRALDF
CYTD_HUMAN    ----------MMWPMHTPLLLLTALMVAVAGSASAQSRTLAGGI---HATDLNDKSVQCALDFA
CYTN_HUMAN    ----------MAQHLSTLLLLATLAVALAWSPKEEDRIIPGGI---YNADLNDEWVQRALHF
CYTS_HUMAN    ----------MARPLCTLLLMATLAGALASSSKEENRIIPGGI---YDADLNDEWVQRALHF
CYTS_RAT      --------------ISTDYLYISFEHETLSCLGHFLGGI----EKSSMEEEGASEALNY
CYTT_HUMAN    ----------MAWPLCTLLLLLATQAVALAWSPQEEDRIIEGGI----YDADLNDERVQRALHF
CYTX_ONCVO    MLTIKDGTLLIHLLLFSVVALVQLQGAKSARAKNPSKMESKTGENQDRPVLLGGW---EDRDPKDEEILELLPS
CYT_BITAR     ------------------------------------------------IPGGL---SPRDVTDPDVQEAAAF
CYTL_DROME    -------------MNVVKSLCIIGLVLVSLIATQAADEQVVGGV----SQLEGNSRKEALELLD
CYTA_SARPE    ------------MKYVLILCVITLATVAYAQPQCVGCP----SEVKGDKLKQSEETLN
```

FIG. 1B

```
               76::::::86::::::96:::::106:::::116:::::126:::::136:::::146::
CYTA_HUMAN     VKPQLEEKTNETY--GKLEAVQYKTQVVAGTNYY--KVRAGD-------------------NK
CYTA_RAT       VKRQLEEKTNEKY--EKFKVVEYKSQVVAGQILF--KVDVGN-------------------GR
CYTB_RAT       VKSQLEEKANQKF--DVFKAISFRRQVVAGTNFF--KVDVGE-------------------EK
CYTB_BOVIN     VKSQLEEKENKKF--PVFKALEFKSQLVAGKNYF--KVQVDE-------------------DD
CYT1_MOUSE     VRPLLEEQTNEKY--EKFEAVEYKSQVVAGQNLF--KIDVGN-------------------GC
CYT2_MOUSE     VRPLLEEKTNEKY--EKFKAIEYKVQVVQGLNYF--KMNVGR-------------------GC
CYT3_MOUSE     VRPQLEAKTNKKY--EKFEAVEYKTQVVAGENIF--KMDVGH-------------------GC
CYTB_HUMAN     VRSQLEEKYNKKF--PVFKAVSFKSQVVAGTNYF--KVHVGD-------------------ED
CYT1_ORYZA     AVTEHNKKANSLL--FEKLVSVKQQVVAGTLYYFTIEVKEGD-------------------AK
CYT1_ORYZA-D86 AVTEHNKKANSLL--FEKLVSVKQQVVAGTLYYFTIEVKEGD-------------------AK
CYT2_ORYZA     AVAEHNSKANAML--LERVVKRQQVVGGFMHYLTVEVKEPGG-------------------AN
CYT_COWP       AVEEHNKKQNALL--FGRVVSAQQVVSGTLYTITLEAKDGG--------------------QK
CYT1_MAIZE     AVNEHNQKANALL--FEKLVKAKTQVVAGTMYYLTIEVKDGE-------------------VK
CYT2_MAIZE     AVDEHNKKANALL--FEKLVKAKTQVVAGTMYYLTIEVKDGE-------------------VK
CYT_CHICK      AMAEYNRASNDKYSSRVVRVISAKRQLVSGIKYI--LQVEIGRTTCPKSSGDL-----QSCEFHDEPEMA-KYT
CYTC_BOVIN     AVSEFNKRSNDAYQSRVVRVRVRARKQVVSGMNYF--LDVELGRTTCTKSQANL-----DSCPFHNQPHLK-REK
CYTC_HUMAN     AVGEYNKASNDMYHSRALQVVRARKQIVAGVNYF--LDVELGRTTCTKSQPNL-----DNCPFHDQPHLK-RKA
CYTC_MOUSE     AVSEYNKGSNDAYHSRAIQVVRARKQLVAGVNYF--FDVEMGRTTCTKSQTNL-----TDCPFHDQPHLM-RKA
CYTC_RAT       AVSEYNKGSNDAYHSRAIQVVRARKQLVAGINYY--LDVEMGRTTCTKSQTNL-----TNCPFHDQPHLM-RKA
CYTD_HUMAN     ISEYNKVINKDEYYSRPLQVMAAYQQIVGGVNYY--FNVKFGRTTCTKSQPNL-----DNCPFNDQPKLK-EEE
CYTN_HUMAN     AISEYNKATKDDYYRRPLRVLRVLRAROQTVGGVNYF--FDVEVGRTICTKSQPNL-----DTCAFHEQPELQ-KKQ
CYTS_HUMAN     AISEYNKATEDEYYRRPLQVLRAREQTFGGVNYF--FDVEVGRTICTKSQPNL-----DTCAFHEQPELQ-KKQ
CYTS_RAT       AVNEYNEKNSDLYLSRVVEVKDVQKQVVAGTKFF--FDVILGKTICLKTQGDL-----TNCPLNEEADQQ-EHE
CYTT_HUMAN     VISEYNKATEDEYYRRLLRVLRAREQIVGGVNYF--FDIEVGRTICTKSQPNL-----DTCAFHEQPELQ-KKQ
CYTX_ONCVO     ILMKVNEQSNDEYHLMPIKLLKVSSQVVAGVKYK--MDVQVARSQCKKSSNEK------VDLTKCKKLEGH-PEK
CYT_BITAR      AVEKYNAGSKNDYYFKERRVVEAQSQVVSGVKYY--LMMELLKTTCKKTVGRPKGYQEIQNCN--LPPENQQEEI
CYTL_DROME     ATLAQLATGDGPSY-KAINVTSVTGQVVAGSLNT--YEVELDNGSD------------------KK-
CYTA_SARPE     KSLSKLAAGDGPTY-KLVKINSATTQVVSGSKDV--INADLKDEND-----------------KTK
```

FIG. 1C

```
            151::::::161::::::171::::::181::::::191::::::201::::::211::::::221:::
CYTA_HUMAN        YMHL-KVFKSLPGQNEDLVLTGYQVDKNKDDELTGF
CYTA_RAT          FLHM-KVLRGLSGDDDLKLLDYQTNKTKNDELTDF
CYTB_RAT          CVHL-RVFEPLPHENKPLITLSSYQTDKEKHDELTYF
CYTB_BOVIN        FVHI-RVFESLPHENKPVALTSYQTNKGRHDELTYF
CYT1_MOUSE        FLHM-KVFRGLSGEDDLKLKGYQTNKTKDELTSM
CYT2_MOUSE        YLHI-NVLSGISSENDLELTGYKAKQTNNDELTYF
CYT3_MOUSE        FIHI-KVFNGPTGKDNYELHGYQTDKTMDEELTYF
CYTB_HUMAN        FVHL-RVFQSLPHENKPLTLSNYQTNKAKHDELTYF
CYT1_ORYZA        KLYEAKVWEK-PWMDFKELQEFKPVDASANA
CYT1_ORYZA-D86    KLYEAKVWEK-PWM FKELQEFKPVDASANA
CYT2_ORYZA        KLYEAKVWER-AWENFKQLQDFKPLDDATA
CYT_COWP          KVYEAKVWEK-PWLNFKELQEFKHVGDAPA
CYT1_MAIZE        KLYEAKVWEK-PWENFKQLQEFKPVEEGASA
CYT2_MAIZE        KLYEAKVWEK-PWENFKQLQEFKPVEEGASA
CYT_CHICK         TCTF-VVYSI-PWL-NQIKLLESKC-Q
CYTC_BOVIN        LCSF-QVYVV-PWM-NTINLVKFSC-QD
CYTC_HUMAN        FCSF-QIYAV-PWQ-GTMTLSKSTC-QDA
CYTC_MOUSE        LCSF-QIYSV-PWK-GTHSLTKFSC-KNA
CYTC_RAT          LCSF-QIYSV-PWK-GTHTLTKSSC-KNA
CYTD_HUMAN        FCSF-QINEV-PWE-DKISILNYKC-RKV
CYTN_HUMAN        LCSF-EIYEV-PWE-NRRSLVKSRC-QES
CYTS_HUMAN        LCSF-EIYEV-PWE-DRMSLVNSRC-QEA
CYTS_RAT          FCSF-VVHDI-PWE-NYIVLLSSSC-HSI
CYTT_HUMAN        LCSF-QIYEV-PWE-DRMSLVNSRC-QEA
CYTX_ONCVO        VMTL-EVWEK-PWE-NFMRVEILGT-KEV
CYT_BITAR         TCRF-EVWSR-PWL-PSTSLTK
CYTL_DROME        QCTV-KIWTQ-PWLKENGTNIKIKCSGDDGELDRTW
CYTA_SARPE        TCDI-TIWSQ-PWLENGIEVT FNCPGEPKVVKKHSA
```

FIG. 2

The DNA coding sequence for oryzacystatin-1Δ86.

ATGTCGAGCG ACGGAGGGCC GGTGCTTGGC GGCGTCGAGC CGGTGGGGAA

CGAGAACGAC CTCCACCTCG TCGACCTCGC CCGCTTCGCC GTCACCGAGC

ACAACAAGAA GGCCAATTCT CTTCTAGAGT TCGAGAAGCT TGTGAGTGTG

AGGCAGCAAG TTGTCGCTGG CACTTTGTAC TATTTCACAA TTGAGGTGAA

GGAAGGGGAT GCCAAGAAGC TCTATGAAGC TAAGGTCTGG GAGAAACCAT

GGATG  TT CAAGGAGCTC CAGGAGTTCA AGCCTGTCGA TGCCAGTGCA

AATGCC

FIG. 3

The coding sequence is underlined.

GGCCGAGGCG CATCGCGCAG GGGGAGAAGG GGAGGAGAAG <u>ATGTCGAGCG</u>

<u>ACGGAGGGCC GGTGCTTGGC GGCGTCGAGC CGGTGGGGAA CGAGAACGAC</u>

<u>CTCCACCTCG TCGACCTCGC CCGCTTCGCC GTCACCGAGC ACAACAAGAA</u>

<u>GGCCAATTCT CTTCTAGAGT TCGAGAAGCT TGTGAGTGTG AGGCAGCAAG</u>

<u>TTGTCGCTGG CACTTTGTAC TATTTCACAA TTGAGGTGAA GGAAGGGGAT</u>

<u>GCCAAGAAGC TCTATGAAGC TAAGGTCTGG GAGAAACCAT GGATG  TT</u>

<u>CAAGGAGCTC CAGGAGTTCA AGCCTGTCGA TGCCAGTGCA AATGCC</u>TAAG

GCCCATCTCG ATCCTATGTG TATCAAGTTA TCTTGTTGAT GGGGAATAAT

ATGTTGTGGA TATAGCTATT GGACATGTTA AATTATCCACA TGATAATATG

GCTTGGATAT AAGGATCTCA CACGATAATA TGGCTTGGAT ATATAGCTAT

AAAGATTTAC CTATGGCATA TTCAATGTGT ATTAGTACTA AGTAAGAATG

ATTGCAAGGT GTATTAACTA CAAATATTGC AATAAAGTC CCTGTTAC

Control

Native Cystatin

Engineered Cystatin

SEQUENCE LISTING (1) GENERAL INFORMATION:

(iii) NUMBER OF SEQUENCES: 79

(2) INFORMATION FOR SEQ ID NO:1:

(i) SEQUENCE CHARACTERISTICS:
      (A) LENGTH: 98 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:1:

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
                20                  25                  30

Glu Thr Tyr Gly Lys Leu Glu Ala Val Gln Tyr Lys Thr Gln Val Val
            35                  40                  45

Ala Gly Thr Asn Tyr Tyr Ile Lys Val Arg Ala Gly Asp Asn Lys Tyr
        50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe
```

(2) INFORMATION FOR SEQ ID NO:2:

(i) SEQUENCE CHARACTERISTICS:
      (A) LENGTH: 103 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:2:

Met Asp Pro Gly Thr Thr Gly Ile Val Gly Gly Val Ser Glu Ala Lys
1               5                   10                  15

Pro Ala Thr Pro Glu Ile Gln Glu Val Ala Asp Lys Val Lys Arg Gln
            20                  25                  30

Leu Glu Glu Lys Thr Asn Glu Lys Tyr Glu Lys Phe Lys Val Val Glu
        35                  40                  45

Tyr Lys Ser Gln Val Val Ala Gly Gln Ile Leu Phe Met Lys Val Asp
50                  55                  60

Val Gly Asn Gly Arg Phe Leu His Met Lys Val Leu Arg Gly Leu Ser
65                  70                  75                  80

Gly Asp Asp Asp Leu Lys Leu Leu Asp Tyr Gln Thr Asn Lys Thr Lys
                85                  90                  95

Asn Asp Glu Leu Thr Asp Phe
            100

(2) INFORMATION FOR SEQ ID NO:3:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:3:

Met Met Cys Gly Ala Pro Ser Ala Thr Met Pro Ala Thr Thr Glu Thr
1               5                   10                  15

Gln Glu Ile Ala Asp Lys Val Lys Ser Gln Leu Glu Glu Lys Ala Asn
            20                  25                  30

Gln Lys Phe Asp Val Phe Lys Ala Ile Ser Phe Arg Arg Gln Val Val
        35                  40                  45

Ala Gly Thr Asn Phe Phe Ile Lys Val Asp Val Gly Glu Glu Lys Cys
50                  55                  60

Val His Leu Arg Val Phe Glu Pro Leu Pro His Glu Asn Lys Pro Leu
65                  70                  75                  80

Thr Leu Ser Ser Tyr Gln Thr Asp Lys Glu Lys His Asp Glu Leu Thr
                85                  90                  95

Tyr Phe (2) INFORMATION FOR SEQ ID NO:4:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:4:

Met Met Cys Gly Gly Thr Ser Ala Thr Gln Pro Ala Thr Ala Glu Thr
1               5                   10                  15

Gln Ala Ile Ala Asp Lys Val Lys Ser Gln Leu Glu Glu Lys Glu Asn

```
                    20                  25                  30
Lys Lys Phe Pro Val Phe Lys Ala Leu Glu Phe Lys Ser Gln Leu Val
            35                  40                  45

Ala Gly Lys Asn Tyr Phe Ile Lys Val Gln Val Asp Glu Asp Asp Phe
        50                  55                  60

Val His Ile Arg Val Phe Glu Ser Leu Pro His Glu Asn Lys Pro Val
 65                  70                  75                  80

Ala Leu Thr Ser Tyr Gln Thr Asn Lys Gly Arg His Asp Glu Leu Thr
                85                  90                  95

Tyr Phe (2) INFORMATION FOR SEQ ID NO:5:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:5:

Met Ser Gln Glu Asn Leu Lys Ile Lys Gly Gly Leu Ser Glu Ala Arg
 1               5                  10                  15

Pro Ala Thr Pro Glu Ile Gln Met Ile Ala Asp Lys Val Arg Pro Leu
                20                  25                  30

Leu Glu Glu Gln Thr Asn Glu Lys Tyr Glu Lys Phe Glu Ala Val Glu
            35                  40                  45

Tyr Lys Ser Gln Val Val Ala Gly Gln Asn Leu Phe Ile Lys Ile Asp
        50                  55                  60

Val Gly Asn Gly Cys Phe Leu His Met Lys Val Phe Arg Gly Leu Ser
 65                  70                  75                  80

Gly Glu Asp Asp Leu Lys Leu Lys Gly Tyr Gln Thr Asn Lys Thr Lys
                85                  90                  95

Thr Asp Glu Leu Thr Ser Met
            100

(2) INFORMATION FOR SEQ ID NO:6:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:6:

Met Thr Glu Tyr Thr Ile Glu Ile Ile Gly Gly Leu Ser Glu Ala Arg
 1               5                  10                  15

Pro Ala Thr Ser Glu Ile Gln Glu Ile Ala Asp Lys Val Arg Pro Leu
                20                  25                  30

Leu Glu Glu Lys Thr Asn Glu Lys Tyr Glu Lys Phe Lys Ala Ile Glu
            35                  40                  45

Tyr Lys Val Gln Val Val Gln Gly Leu Asn Tyr Phe Ile Lys Met Asn
        50                  55                  60
```

Val Gly Arg Gly Cys Tyr Leu His Ile Asn Val Leu Ser Gly Ile Ser
65                  70                  75                  80

Ser Glu Asn Asp Leu Glu Leu Thr Gly Tyr Lys Ala Lys Gln Thr Asn
                85                  90                  95

Asn Asp Glu Leu Thr Tyr Phe
            100

(2) INFORMATION FOR SEQ ID NO:7:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:7:

Met Ser Leu Gly Gly Val Ser Glu Ala Ser Arg Ala Thr Pro Glu Ile
1               5                   10                  15

Gln Met Ile Ala Asn Lys Val Arg Pro Gln Leu Glu Ala Lys Thr Asn
                20                  25                  30

Lys Lys Tyr Glu Lys Phe Glu Ala Val Glu Tyr Lys Thr Gln Val Val
            35                  40                  45

Ala Gly Glu Asn Ile Phe Ile Lys Met Asp Val Gly His Gly Cys Phe
        50                  55                  60

Ile His Ile Lys Val Phe Asn Gly Pro Thr Gly Lys Asp Asn Tyr Glu
65                  70                  75                  80

Leu His Gly Tyr Gln Thr Asp Lys Thr Met Asp Glu Glu Leu Thr Tyr
                85                  90                  95

Phe (2) INFORMATION FOR SEQ ID NO:8:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:8:

Met Met Cys Gly Ala Pro Ser Ala Thr Gln Pro Ala Thr Ala Glu Thr
1               5                   10                  15

Gln His Ile Ala Asp Gln Val Arg Ser Gln Leu Glu Glu Lys Tyr Asn
                20                  25                  30

Lys Lys Phe Pro Val Phe Lys Ala Val Ser Phe Lys Ser Gln Val Val
            35                  40                  45

Ala Gly Thr Asn Tyr Phe Ile Lys Val His Val Gly Asp Glu Asp Phe
        50                  55                  60

Val His Leu Arg Val Phe Gln Ser Leu Pro His Glu Asn Lys Pro Leu
65                  70                  75                  80

Thr Leu Ser Asn Tyr Gln Thr Asn Lys Ala Lys His Asp Glu Leu Thr
                85                  90                  95

Tyr Phe (2) INFORMATION FOR SEQ ID NO:9:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:9:

```
Met Ser Ser Asp Gly Gly Pro Val Leu Gly Val Glu Pro Val Gly
1               5                   10                  15

Asn Glu Asn Asp Leu His Leu Val Asp Leu Ala Arg Phe Ala Val Thr
                20                  25                  30

Glu His Asn Lys Lys Ala Asn Ser Leu Leu Glu Phe Glu Lys Leu Val
            35                  40                  45

Ser Val Lys Gln Gln Val Val Ala Gly Thr Leu Tyr Tyr Phe Thr Ile
    50                  55                  60

Glu Val Lys Glu Gly Asp Ala Lys Lys Leu Tyr Glu Ala Lys Val Trp
65                  70                  75                  80

Glu Lys Pro Trp Met Asp Phe Lys Glu Leu Gln Glu Phe Lys Pro Val
                85                  90                  95

Asp Ala Ser Ala Asn Ala
            100
```

(2) INFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:10:

```
Met Ser Ser Asp Gly Gly Pro Val Leu Gly Val Glu Pro Val Gly
1               5                   10                  15

Asn Glu Asn Asp Leu His Leu Val Asp Leu Ala Arg Phe Ala Val Thr
                20                  25                  30

Glu His Asn Lys Lys Ala Asn Ser Leu Leu Glu Phe Glu Lys Leu Val
            35                  40                  45

Ser Val Lys Gln Gln Val Val Ala Gly Thr Leu Tyr Tyr Phe Thr Ile
    50                  55                  60

Glu Val Lys Glu Gly Asp Ala Lys Lys Leu Tyr Glu Ala Lys Val Trp
65                  70                  75                  80

Glu Lys Pro Trp Met Phe Lys Glu Leu Gln Glu Phe Lys Pro Val Asp
                85                  90                  95

Ala Ser Ala Asn Ala
            100
```

(2) INFORMATION FOR SEQ ID NO:11:

(i) SEQUENCE CHARACTERISTICS:
        (A) LENGTH: 107 amino acids
        (B) TYPE: amino acid
        (C) STRANDEDNESS: single (D) TOPOLOGY: linear (ii) MOLECULE TYPE: protein (iii) HYPOTHETICAL: NO (xi) SEQUENCE DESCRIPTION: SEQ ID NO:11:

```
Met Ala Glu Glu Ala Gln Ser His Ala Arg Glu Gly Gly Arg His Pro
1               5                   10                  15

Arg Gln Pro Ala Gly Arg Glu Asn Asp Leu Thr Thr Val Glu Leu Ala
            20                  25                  30

Arg Phe Ala Val Ala Glu His Asn Ser Lys Ala Asn Ala Met Leu Glu
            35                  40                  45

Leu Glu Arg Val Val Lys Val Arg Gln Gln Val Val Gly Gly Phe Met
50                      55                  60

His Tyr Leu Thr Val Glu Val Lys Glu Pro Gly Gly Ala Asn Lys Leu
65                  70                  75                  80

Tyr Glu Ala Lys Val Trp Glu Arg Ala Trp Glu Asn Phe Lys Gln Leu
                85                  90                  95

Gln Asp Phe Lys Pro Leu Asp Asp Ala Thr Ala
            100                 105
```

(2) INFORMATION FOR SEQ ID NO:12:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:12:

```
Met Ala Ala Leu Gly Gly Asn Arg Asp Val Ala Gly Asn Gln Asn Ser
1               5                   10                  15

Leu Glu Ile Asp Ser Leu Ala Arg Phe Ala Val Glu Glu His Asn Lys
            20                  25                  30

Lys Gln Asn Ala Leu Leu Glu Phe Gly Arg Val Val Ser Ala Gln Gln
            35                  40                  45

Gln Val Val Ser Gly Thr Leu Tyr Thr Ile Thr Leu Glu Ala Lys Asp
50                      55                  60

Gly Gly Gln Lys Lys Val Tyr Glu Ala Lys Val Trp Glu Lys Pro Trp
65                  70                  75                  80

Leu Asn Phe Lys Glu Leu Gln Glu Phe Lys His Val Gly Asp Ala Pro
                85                  90                  95

Ala
```

(2) INFORMATION FOR SEQ ID NO:13:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:13:

```
Met Arg Lys His Arg Ile Val Ser Leu Val Ala Ala Leu Leu Val Leu
  1               5                  10                  15

Leu Ala Leu Ala Ala Val Ser Ser Thr Arg Ser Thr Gln Lys Glu Ser
             20                  25                  30

Val Ala Asp Asn Ala Gly Met Leu Ala Gly Gly Ile Lys Asp Val Pro
             35                  40                  45

Ala Asn Glu Asn Asp Leu Gln Leu Gln Glu Leu Ala Arg Phe Ala Val
     50                  55                  60

Asn Glu His Asn Gln Lys Ala Asn Ala Leu Leu Gly Phe Glu Lys Leu
 65                  70                  75                  80

Val Lys Ala Lys Thr Gln Val Val Ala Gly Thr Met Tyr Tyr Leu Thr
                 85                  90                  95

Ile Glu Val Lys Asp Gly Glu Val Lys Lys Leu Tyr Glu Ala Lys Val
                 100                 105                 110

Trp Glu Lys Pro Trp Glu Asn Phe Lys Gln Leu Gln Glu Phe Lys Pro
             115                 120                 125

Val Glu Glu Gly Ala Ser Ala
            130                 135

(2) INFORMATION FOR SEQ ID NO:14:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:14:

Met Arg Leu His Arg Ile Val Ser Leu Val Ala Ala Leu Leu Ile Leu
 1                5                   10                  15

Leu Ala Leu Ala Val Ser Ser Thr Arg Asn Ala Gln Glu Asp Ser Met
             20                  25                  30

Ala Asp Asn Thr Gly Thr Leu Ala Gly Gly Ile Lys Asp Val Pro Gly
             35                  40                  45

Asn Glu Asn Asp Leu His Leu Gln Glu Leu Ala Arg Phe Ala Val Asp
     50                  55                  60

Glu His Asn Lys Lys Ala Asn Ala Leu Leu Gly Phe Glu Lys Leu Val
 65                  70                  75                  80

Lys Ala Lys Thr Gln Val Val Ala Gly Thr Met Tyr Tyr Leu Thr Ile
                 85                  90                  95

Glu Val Lys Asp Gly Glu Val Lys Lys Leu Tyr Glu Ala Lys Val Trp
                 100                 105                 110

Glu Lys Pro Trp Glu Asn Phe Lys Glu Leu Gln Glu Phe Lys Pro Val
             115                 120                 125

Glu Glu Gly Ala Ser Ala
            130

(2) INFORMATION FOR SEQ ID NO:15:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein
```

(iii) HYPOTHETICAL: NO (xi) SEQUENCE DESCRIPTION: SEQ ID NO:15:

```
Met Ala Gly Ala Arg Gly Cys Val Val Leu Ala Ala Leu Met
1               5                  10                  15

Leu Val Gly Ala Val Leu Gly Ser Glu Asp Arg Ser Arg Leu Leu Gly
                20                  25                  30

Ala Pro Val Pro Val Asp Glu Asn Asp Glu Gly Leu Gln Arg Ala Leu
                35                  40                  45

Gln Phe Ala Met Ala Glu Tyr Asn Arg Ala Ser Asn Asp Lys Tyr Ser
50                  55                  60

Ser Arg Val Val Arg Val Ile Ser Ala Lys Arg Gln Leu Val Ser Gly
65                  70                  75                  80

Ile Lys Tyr Ile Leu Gln Val Glu Ile Gly Arg Thr Thr Cys Pro Lys
                85                  90                  95

Ser Ser Gly Asp Leu Gln Ser Cys Glu Phe His Asp Glu Pro Glu Met
                100                 105                 110

Ala Lys Tyr Thr Thr Cys Thr Phe Val Val Tyr Ser Ile Pro Trp Leu
                115                 120                 125

Asn Gln Ile Lys Leu Leu Glu Ser Lys Cys Gln
                130                 135
```

(2) INFORMATION FOR SEQ ID NO:16:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:16:

```
Arg Leu Leu Gly Gly Leu Met Glu Ala Asp Val Asn Glu Glu Gly Val
1               5                   10                  15

Gln Glu Ala Leu Ser Phe Ala Val Ser Glu Phe Asn Lys Arg Ser Asn
                20                  25                  30

Asp Ala Tyr Gln Ser Arg Val Val Arg Val Val Arg Ala Arg Lys Gln
                35                  40                  45

Val Val Ser Gly Met Asn Tyr Phe Leu Asp Val Glu Leu Gly Arg Thr
50                  55                  60

Thr Cys Thr Lys Ser Gln Ala Asn Leu Asp Ser Cys Pro Phe His Asn
65                  70                  75                  80

Gln Pro His Leu Lys Arg Glu Lys Leu Cys Ser Phe Gln Val Tyr Val
                85                  90                  95

Val Pro Trp Met Asn Thr Ile Asn Leu Val Lys Phe Ser Cys Gln Asp
                100                 105                 110
```

(2) INFORMATION FOR SEQ ID NO:17:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:17:

```
Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Gly
            35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
                100                 105                 110

Asp Gln Pro His Leu Lys Arg Lys Ala Phe Cys Ser Phe Gln Ile Tyr
            115                 120                 125

Ala Val Pro Trp Gln Gly Thr Met Thr Leu Ser Lys Ser Thr Cys Gln
            130                 135                 140

Asp Ala
145
```

(2) INFORMATION FOR SEQ ID NO:18:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:18:

```
Met Ala Ser Pro Leu Arg Ser Leu Leu Phe Leu Leu Ala Val Leu Gly
1               5                   10                  15

Val Ala Trp Ala Ala Thr Pro Lys Gln Gly Pro Arg Met Leu Gly Ala
            20                  25                  30

Pro Glu Glu Ala Asp Ala Asn Glu Glu Gly Val Arg Arg Ala Leu Asp
            35                  40                  45

Phe Ala Val Ser Glu Tyr Asn Lys Gly Ser Asn Asp Ala Tyr His Ser
    50                  55                  60

Arg Ala Ile Gln Val Val Arg Ala Arg Lys Gln Leu Val Ala Gly Val
65                  70                  75                  80

Asn Tyr Phe Phe Asp Val Glu Met Gly Arg Thr Thr Cys Thr Lys Ser
                85                  90                  95

Gln Thr Asn Leu Thr Asp Cys Pro Phe His Asp Gln Pro His Leu Met
                100                 105                 110

Arg Lys Ala Leu Cys Ser Phe Gln Ile Tyr Ser Val Pro Trp Lys Gly
            115                 120                 125

Thr His Ser Leu Thr Lys Phe Ser Cys Lys Asn Ala
            130                 135                 140
```

(2) INFORMATION FOR SEQ ID NO:19:

(i) SEQUENCE CHARACTERISTICS:
      (A) LENGTH: 127 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:19:

```
Val Leu Ala Val Ala Trp Ala Gly Thr Ser Arg Pro Pro Arg Leu
1               5                   10                  15

Leu Gly Ala Pro Gln Glu Ala Asp Ala Ser Glu Glu Gly Val Gln Arg
            20                  25                  30

Ala Leu Asp Phe Ala Val Ser Glu Tyr Asn Lys Gly Ser Asn Asp Ala
            35                  40                  45

Tyr His Ser Arg Ala Ile Gln Val Val Arg Ala Arg Lys Gln Leu Val
50                  55                  60

Ala Gly Ile Asn Tyr Tyr Leu Asp Val Glu Met Gly Arg Thr Thr Cys
65                  70                  75                  80

Thr Lys Ser Gln Thr Asn Leu Thr Asn Cys Pro Phe His Asp Gln Pro
                85                  90                  95

His Leu Met Arg Lys Ala Leu Cys Ser Phe Gln Ile Tyr Ser Val Pro
                100                 105                 110

Trp Lys Gly Thr His Thr Leu Thr Lys Ser Ser Cys Lys Asn Ala
            115                 120                 125
```

(2) INFORMATION FOR SEQ ID NO:20:

(i) SEQUENCE CHARACTERISTICS:
      (A) LENGTH: 142 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:20:

```
Met Met Trp Pro Met His Thr Pro Leu Leu Leu Thr Ala Leu Met
1               5                   10                  15

Val Ala Val Ala Gly Ser Ala Ser Ala Gln Ser Arg Thr Leu Ala Gly
            20                  25                  30

Gly Ile His Ala Thr Asp Leu Asn Asp Lys Ser Val Gln Cys Ala Leu
            35                  40                  45

Asp Phe Ala Ile Ser Glu Tyr Asn Lys Val Ile Asn Lys Asp Glu Tyr
            50                  55                  60

Tyr Ser Arg Pro Leu Gln Val Met Ala Ala Tyr Gln Gln Ile Val Gly
65                  70                  75                  80

Gly Val Asn Tyr Tyr Phe Asn Val Lys Phe Gly Arg Thr Thr Cys Thr
            85                  90                  95

Lys Ser Gln Pro Asn Leu Asp Asn Cys Pro Phe Asn Asp Gln Pro Lys
                100                 105                 110

Leu Lys Glu Glu Glu Phe Cys Ser Phe Gln Ile Asn Glu Val Pro Trp
            115                 120                 125

Glu Asp Lys Ile Ser Ile Leu Asn Tyr Lys Cys Arg Lys Val
            130                 135                 140
```

(2) INFORMATION FOR SEQ ID NO:21:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:21:

```
Met Ala Gln His Leu Ser Thr Leu Leu Leu Leu Ala Thr Leu Ala
1               5                  10                  15

Val Ala Leu Ala Trp Ser Pro Lys Glu Glu Asp Arg Ile Ile Pro Gly
            20                  25                  30

Gly Ile Tyr Asn Ala Asp Leu Asn Asp Glu Trp Val Gln Arg Ala Leu
        35                  40                  45

His Phe Ala Ile Ser Glu Tyr Asn Lys Ala Thr Lys Asp Asp Tyr Tyr
    50                  55                  60

Arg Arg Pro Leu Arg Val Leu Arg Ala Arg Gln Gln Thr Val Gly Gly
65                  70                  75                  80

Val Asn Tyr Phe Phe Asp Val Glu Val Gly Arg Thr Ile Cys Thr Lys
            85                  90                  95

Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
            115                 120                 125

Asn Arg Arg Ser Leu Val Lys Ser Arg Cys Gln Glu Ser
            130                 135                 140
```

(2) INFORMATION FOR SEQ ID NO:22:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:22:

```
Met Ala Arg Pro Leu Cys Thr Leu Leu Leu Met Ala Thr Leu Ala
1               5                  10                  15

Gly Ala Leu Ala Ser Ser Ser Lys Glu Glu Asn Arg Ile Ile Pro Gly
            20                  25                  30

Gly Ile Tyr Asp Ala Asp Leu Asn Asp Glu Trp Val Gln Arg Ala Leu
        35                  40                  45

His Phe Ala Ile Ser Glu Tyr Asn Lys Ala Thr Glu Asp Glu Tyr Tyr
    50                  55                  60

Arg Arg Pro Leu Gln Val Leu Arg Ala Arg Glu Gln Thr Phe Gly Gly
65                  70                  75                  80

Val Asn Tyr Phe Phe Asp Val Glu Val Gly Arg Thr Ile Cys Thr Lys
            85                  90                  95

Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
            115                 120                 125
```

```
Asp Arg Met Ser Leu Val Asn Ser Arg Cys Gln Glu Ala
    130                 135                 140
```

(2) INFORMATION FOR SEQ ID NO:23:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:23:

```
Ile Ser Thr Asp Tyr Leu Tyr Ile Ser Phe Glu His Glu Thr Leu Ser
1               5                   10                  15

Cys Leu Gly His Phe Leu Gly Gly Ile Glu Lys Ser Ser Met Glu Glu
            20                  25                  30

Glu Gly Ala Ser Glu Ala Leu Asn Tyr Ala Val Asn Glu Tyr Asn Glu
        35                  40                  45

Lys Asn Ser Asp Leu Tyr Leu Ser Arg Val Val Glu Val Lys Asp Val
    50                  55                  60

Gln Lys Gln Val Val Ala Gly Thr Lys Phe Phe Asp Val Ile Leu
65                  70                  75                  80

Gly Lys Thr Ile Cys Leu Lys Thr Gln Gly Asp Leu Thr Asn Cys Pro
                85                  90                  95

Leu Asn Glu Glu Ala Asp Gln Gln Glu His Glu Phe Cys Ser Phe Val
                100                 105                 110

Val His Asp Ile Pro Trp Glu Asn Tyr Ile Val Leu Leu Ser Ser Ser
        115                 120                 125

Cys His Ser Ile
    130
```

(2) INFORMATION FOR SEQ ID NO:24:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:24:

```
Met Ala Trp Pro Leu Cys Thr Leu Leu Leu Leu Ala Thr Gln Ala
1               5                   10                  15

Val Ala Leu Ala Trp Ser Pro Gln Glu Glu Asp Arg Ile Ile Glu Gly
            20                  25                  30

Gly Ile Tyr Asp Ala Asp Leu Asn Asp Glu Arg Val Gln Arg Ala Leu
        35                  40                  45

His Phe Val Ile Ser Glu Tyr Asn Lys Ala Thr Glu Asp Glu Tyr Tyr
    50                  55                  60

Arg Arg Leu Leu Arg Val Leu Arg Ala Arg Glu Gln Ile Val Gly Gly
65                  70                  75                  80

Val Asn Tyr Phe Phe Asp Ile Glu Val Gly Arg Thr Ile Cys Thr Lys
                85                  90                  95
```

```
Ser Gln Pro Asn Leu Asp Thr Cys Ala Phe His Glu Gln Pro Glu Leu
            100                 105                 110

Gln Lys Lys Gln Leu Cys Ser Phe Gln Ile Tyr Glu Val Pro Trp Glu
        115                 120                 125

Asp Arg Met Ser Leu Val Asn Ser Arg Cys Gln Glu Ala
    130                 135                 140
```

(2) INFORMATION FOR SEQ ID NO:25:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:25:

```
Met Leu Thr Ile Lys Asp Gly Thr Leu Leu Ile His Leu Leu Leu Phe
1               5                   10                  15

Ser Val Val Ala Leu Val Gln Leu Gln Gly Ala Lys Ser Ala Arg Ala
            20                  25                  30

Lys Asn Pro Ser Lys Met Glu Ser Lys Thr Gly Glu Asn Gln Asp Arg
        35                  40                  45

Pro Val Leu Leu Gly Gly Trp Glu Asp Arg Asp Pro Lys Asp Glu Glu
    50                  55                  60

Ile Leu Glu Leu Leu Pro Ser Ile Leu Met Lys Val Asn Glu Gln Ser
65                  70                  75                  80

Asn Asp Glu Tyr His Leu Met Pro Ile Lys Leu Leu Lys Val Ser Ser
                85                  90                  95

Gln Val Val Ala Gly Val Lys Tyr Lys Met Asp Val Gln Val Ala Arg
            100                 105                 110

Ser Gln Cys Lys Lys Ser Ser Asn Glu Lys Val Asp Leu Thr Lys Cys
        115                 120                 125

Lys Lys Leu Glu Gly His Pro Glu Lys Val Met Thr Leu Glu Val Trp
    130                 135                 140

Glu Lys Pro Trp Glu Asn Phe Met Arg Val Glu Ile Leu Gly Thr Lys
145                 150                 155                 160

Glu Val
```

(2) INFORMATION FOR SEQ ID NO:26:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:26:

```
Ile Pro Gly Gly Leu Ser Pro Arg Asp Val Thr Asp Pro Asp Val Gln
1               5                   10                  15

Glu Ala Ala Ala Phe Ala Val Glu Lys Tyr Asn Ala Gly Ser Lys Asn
            20                  25                  30

Asp Tyr Tyr Phe Lys Glu Arg Arg Val Val Glu Ala Gln Ser Gln Val
        35                  40                  45
```

```
Val Ser Gly Val Lys Tyr Tyr Leu Met Met Glu Leu Leu Lys Thr Thr
    50                  55                  60

Cys Lys Lys Thr Val Gly Arg Pro Lys Gly Tyr Gln Glu Ile Gln Asn
 65                  70                  75                  80

Cys Asn Leu Pro Pro Glu Asn Gln Gln Glu Ile Thr Cys Arg Phe
                 85                  90                  95

Glu Val Trp Ser Arg Pro Trp Leu Pro Ser Thr Ser Leu Thr Lys
                100                 105                 110
```

(2) INFORMATION FOR SEQ ID NO:27:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:27:

```
Met Asn Val Val Lys Ser Leu Cys Ile Leu Gly Leu Val Leu Val Ser
 1               5                  10                  15

Leu Ile Ala Thr Gln Ala Ala Asp Glu Gln Val Val Gly Gly Val Ser
                20                  25                  30

Gln Leu Glu Gly Asn Ser Arg Lys Glu Ala Leu Glu Leu Leu Asp Ala
            35                  40                  45

Thr Leu Ala Gln Leu Ala Thr Gly Asp Gly Pro Ser Tyr Lys Ala Ile
 50                  55                  60

Asn Val Thr Ser Val Thr Gly Gln Val Val Ala Gly Ser Leu Asn Thr
 65                  70                  75                  80

Tyr Glu Val Glu Leu Asp Asn Gly Ser Asp Lys Lys Gln Cys Thr Val
                 85                  90                  95

Lys Ile Trp Thr Gln Pro Trp Leu Lys Glu Asn Gly Thr Asn Ile Lys
                100                 105                 110

Ile Lys Cys Ser Gly Asp Asp Gly Glu Leu Asp Arg Thr Trp
            115                 120                 125
```

(2) INFORMATION FOR SEQ ID NO:28:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:28:

```
Met Lys Tyr Val Leu Ile Leu Cys Val Ile Thr Leu Ala Thr Val Ala
 1               5                  10                  15

Tyr Ala Gln Pro Gln Cys Val Gly Cys Pro Ser Glu Val Lys Gly Asp
                20                  25                  30

Lys Leu Lys Gln Ser Glu Glu Thr Leu Asn Lys Ser Leu Ser Lys Leu
            35                  40                  45

Ala Ala Gly Asp Gly Pro Thr Tyr Lys Leu Val Lys Ile Asn Ser Ala
 50                  55                  60
```

```
Thr Thr Gln Val Val Ser Gly Ser Lys Asp Val Ile Asn Ala Asp Leu
65                  70                  75                  80

Lys Asp Glu Asn Asp Lys Thr Lys Thr Cys Asp Ile Thr Ile Trp Ser
            85                  90                  95

Gln Pro Trp Leu Glu Asn Gly Ile Glu Val Thr Phe Asn Cys Pro Gly
            100                 105                 110

Glu Pro Lys Val Val Lys Lys His Ser Ala
        115                 120
```

(2) INFORMATION FOR SEQ ID NO:29:

(i) SEQUENCE CHARACTERISTICS:
        (A) LENGTH: 303 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:29:

```
ATGTCGAGCG ACGGAGGGCC GGTGCTTGGC GGCGTCGAGC CGGTGGGGAA CGAGAACGAC    60

CTCCACCTCG TCGACCTCGC CCGCTTCGCC GTCACCGAGC ACAACAAGAA GGCCAATTCT   120

CTTCTAGAGT TCGAGAAGCT TGTGAGTGTG AGGCAGCAAG TTGTCGCTGG CACTTTGTAC   180

TATTTCACAA TTGAGGTGAA GGAAGGGGAT GCCAAGAAGC TCTATGAAGC TAAGGTCTGG   240

GAGAAACCAT GGATGTTCAA GGAGCTCCAG GAGTTCAAGC CTGTCGATGC CAGTGCAAAT   300

GCC                                                                 303
```

(2) INFORMATION FOR SEQ ID NO:30:

(i) SEQUENCE CHARACTERISTICS:
        (A) LENGTH: 596 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:30:

```
GGCCGAGGCG CATCGCGCAG GGGGAGAAGG GGAGGAGAAG ATGTCGAGCG ACGGAGGGCC    60

GGTGCTTGGC GGCGTCGAGC CGGTGGGGAA CGAGAACGAC CTCCACCTCG TCGACCTCGC   120

CCGCTTCGCC GTCACCGAGC ACAACAAGAA GGCCAATTCT CTTCTAGAGT TCGAGAAGCT   180

TGTGAGTGTG AGGCAGCAAG TTGTCGCTGG CACTTTGTAC TATTTCACAA TTGAGGTGAA   240

GGAAGGGGAT GCCAAGAAGC TCTATGAAGC TAAGGTCTGG GAGAAACCAT GGATGTTCAA   300

GGAGCTCCAG GAGTTCAAGC CTGTCGATGC CAGTGCAAAT GCCTAAGGCC CATCTCGATC   360

CTATGTGTAT CAAGTTATCT TGTTGATGGG AATAATATG TTGTGGATAT AGCTATTGGA   420

CATGTTAAAT TATCCACATG ATAATATGGC TTGGATATAA GGATCTCACA CGATAATATG   480

GCTTGGATAT ATAGCTATAA AGATTTACCT ATGGCATATT CAATGTGTAT TAGTACTAAG   540

TAAGAATGAT TGCAAGGTGT ATTAACTACA AATATTGCAA TAAAAGTCCC TGTTAC       596
```

(2) INFORMATION FOR SEQ ID NO:31:

(i) SEQUENCE CHARACTERISTICS:
        (A) LENGTH: 31 base pairs (B) TYPE: nucleic acid
    (C) STRANDEDNESS: single
    (D) TOPOLOGY: linear (ii) MOLECULE TYPE: other nucleic acid
      (A) DESCRIPTION: /desc = "PRIMER"

(iii) HYPOTHETICAL: NO (xi) SEQUENCE DESCRIPTION: SEQ ID NO:31:

ACATGTCGAA TTCTTAGGCA TTTGCACTGG C                              31

(2) INFORMATION FOR SEQ ID NO:32:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "PRIMER"

(iii) HYPOTHETICAL: NO (xi) SEQUENCE DESCRIPTION: SEQ ID NO:32:

GAGGAGCCCG GGTCGAGCGA CGGA                                      24

(2) INFORMATION FOR SEQ ID NO:33:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "PRIMER"

(iii) HYPOTHETICAL: NO (xi) SEQUENCE DESCRIPTION: SEQ ID NO:33:

CTCGAACTCT AGAAGAGAAT TGGCCTTGTT GTG                             33

(2) INFORMATION FOR SEQ ID NO:34:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "PRIMER"

(iii) HYPOTHETICAL: NO (xi) SEQUENCE DESCRIPTION: SEQ ID NO:34:

AATTCTCTTC TAGAGTTC                                             18

(2) INFORMATION FOR SEQ ID NO:35:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "PRIMER"

(iii) HYPOTHETICAL: NO (xi) SEQUENCE DESCRIPTION: SEQ ID NO:35:

CACGTGAATT CATGAAGTTC CTTATCCTTA CCGCGCTCTG CGC          43

(2) INFORMATION FOR SEQ ID NO:36:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (xi) SEQUENCE DESCRIPTION: SEQ ID NO:36:

CACGGCCTGC AGTTAGACCT TGGCCTTTCC GGCGACAACT GC          42

(2) INFORMATION FOR SEQ ID NO:37:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (xi) SEQUENCE DESCRIPTION: SEQ ID NO:37:

GAACAGCGTA GGCAGAGACT CCGAAGTGCT TGTCCTTGGC GT          42

(2) INFORMATION FOR SEQ ID NO:38:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (xi) SEQUENCE DESCRIPTION: SEQ ID NO:38:

GAGTCTCTGC CTACGCTGTT C                                 21

(2) INFORMATION FOR SEQ ID NO:39:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (xi) SEQUENCE DESCRIPTION: SEQ ID NO:39:

ACTATGGATC CGCAGCACTC GGTGGCAATC G                      31

(2) INFORMATION FOR SEQ ID NO:40:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:40:

ATATTAAGCT TACACTATGC AGGTGCATTC CC          32

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:41:

CTTGGCGGCG TCCCGGTGGG GAAC          24

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:42:

AAACCATGGA TGTTCAAGGA GCTC          24

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:43:

AAACCATGGG ACTTCAAGCC T          21

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "PRIMER"

(iii) HYPOTHETICAL: NO (xi) SEQUENCE DESCRIPTION: SEQ ID NO:44:

GAGAAACCAA ACATGGACTT C                                              21

(2) INFORMATION FOR SEQ ID NO:45:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (xi) SEQUENCE DESCRIPTION: SEQ ID NO:45:

GAGAAACCAG CGATGGACTT C                                              21

(2) INFORMATION FOR SEQ ID NO:46:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (xi) SEQUENCE DESCRIPTION: SEQ ID NO:46:

TGGGAGAAAG CATGGATGGA C                                              21

(2) INFORMATION FOR SEQ ID NO:47:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (xi) SEQUENCE DESCRIPTION: SEQ ID NO:47:

AAGGAGCTCC TGGAGTTCAA G                                              21

(2) INFORMATION FOR SEQ ID NO:48:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (xi) SEQUENCE DESCRIPTION: SEQ ID NO:48:

```
GACTTCAAGA TACTCCAGGA G                                              21

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:49:

TGGGAGAAAC TGCCATGGAT G                                              21

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:50:

AAGCTCTATG AAAAGGTCTG G                                              21

(2) INFORMATION FOR SEQ ID NO:51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:51:

GTCTGGGAGA AATAGTGGAT GGACTTCAAC GAACTCCAG                            39

(2) INFORMATION FOR SEQ ID NO:52:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:52:

GTCTGGGAGA AACCATAGAT GGACTTCAAC GAACTCCAG                            39

(2) INFORMATION FOR SEQ ID NO:53:

(i) SEQUENCE CHARACTERISTICS:
```

(A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:53:

GTCTGGGAGA AACCATGGAT GTAGTTCAAC GAACTCCAG                          39

(2) INFORMATION FOR SEQ ID NO:54:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:54:

GATCCGATGA CGATGACAAA CACCTCGTC                                    29

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:55:

GACGAGGTGT TTGTCATCGT CATC                                         24

(2) INFORMATION FOR SEQ ID NO:56:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:56:

Gln Val Val Ala Gly
1               5

(2) INFORMATION FOR SEQ ID NO:57:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:57:

Gln Leu Val Ala Gly
1               5

(2) INFORMATION FOR SEQ ID NO:58:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:58:

Asp Asp Asp Asp Lys
1               5

(2) INFORMATION FOR SEQ ID NO:59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:59:

Ser Glu Asp Arg Ser Arg Leu Leu Gly Ala Pro Val Pro Val Asp
1               5                   10                  15

(2) INFORMATION FOR SEQ ID NO:60:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:60:

Tyr Ser Ser Arg Val Val Arg Val Ile Ser Ala Lys Arg Gln Leu Val
1               5                   10                  15

Ser Gly Ile Lys Tyr Ile Leu Gln
                20

(2) INFORMATION FOR SEQ ID NO:61:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:61:

```
Phe Val Val Tyr Ser Ile Pro Trp Leu Asn Gln Ile Lys Leu Leu Glu
1               5                   10                  15
Ser Lys Cys Gln
            20
```

(2) INFORMATION FOR SEQ ID NO:62:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:62:

```
Arg Gln Leu Val Ser Gly Ile Lys Tyr
1               5
```

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:63:

```
Ser Ile Pro Trp Leu Asn Gln
1               5
```

(2) INFORMATION FOR SEQ ID NO:64:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:64:

```
AGCGAGGACC GCTCCCGGCT CCTGGGGGCT CCA                              33
```

(2) INFORMATION FOR SEQ ID NO:65:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:65:

```
GTCGTCGTTC TCATCTACAG GCACTGGAGC CCCCAG                           36
```

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:66:

GAGAACGACC TCCACCTCGT C                                              21

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:67:

GGCATTTGCA CTGGCATCGA C                                              21

(2) INFORMATION FOR SEQ ID NO:68:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:68:

AAGGCCAATT CTCTTTACTC CAGCCGGGTG GTGCGGGTCA TC                        42

(2) INFORMATION FOR SEQ ID NO:69:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:69:

CACGAGCTGC CGCTTGGCGC TGATGACCCG CAC                                 33

(2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "Primer"

(iii) HYPOTHETICAL: NO (xi) SEQUENCE DESCRIPTION: SEQ ID NO:70:

CGGCAGCTCG TGTCTGGAAT CAAGTACATC                                30

(2) INFORMATION FOR SEQ ID NO:71:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(iii) HYPOTHETICAL: NO (xi) SEQUENCE DESCRIPTION: SEQ ID NO:71:

ATCCCCTTCC TTCACCTGCA GGATGTACTT GATTCCAGA                      39

(2) INFORMATION FOR SEQ ID NO:72:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(iii) HYPOTHETICAL: NO (xi) SEQUENCE DESCRIPTION: SEQ ID NO:72:

ATGTCGAGCG ACGGAGGGCC GGTG                                      24

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(iii) HYPOTHETICAL: NO (xi) SEQUENCE DESCRIPTION: SEQ ID NO:73:

AAGAGAATTG GCCTTCTTGT T                                         21

(2) INFORMATION FOR SEQ ID NO:74:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(iii) HYPOTHETICAL: NO (xi) SEQUENCE DESCRIPTION: SEQ ID NO:74:

```
GTGAAGGAAG GGGATGCCAA GAAG                                              24
```

(2) INFORMATION FOR SEQ ID NO:75:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:75:

```
GCCAAGAAGC TCTATTTTGT AGTGTACAGT ATTCCTTGGC TA                          42
```

(2) INFORMATION FOR SEQ ID NO:76:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:76:

```
CTGGCACTTG CTTTCCAGCA GTTTAATTTG GTTTAGCCAA GGAAT                       45
```

(2) INFORMATION FOR SEQ ID NO:77:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:77:

```
ATAGAGCTTC TTGGCATCCC CTTCCTT                                           27
```

(2) INFORMATION FOR SEQ ID NO:78:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:78:

```
AAGGTCTGGT CGATACCATG GCTGAACCAA AAGGAGCCT                              39
```

(2) INFORMATION FOR SEQ ID NO:79:

(i) SEQUENCE CHARACTERISTICS:

```
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:79:

AGTGTGAGGC GGCAACTTGT CTCTGGCATT AAGTACTACT TCACA                45
```

MODIFIED PROTEINASE INHIBITORS

The invention relates to proteinase inhibitors and in particular novel proteinase inhibitors, methods for producing such inhibitors and products and processors including such inhibitors.

Proteinases are enzymes that break down proteins, their substrate specificity varies considerably and therefore does not form a basis for the purpose of classification. Rather, typically, these enzymes are classified according to the nature of the catalytic reaction that each undertakes. Thus proteinases are divided into four groups termed serine proteinases, cysteine proteinases, aspartic proteinases and metalloproteinases. Serine proteinases and cysteine proteinases are both widespread and diverse and are found in both prokaryotic and eukaryotic organisms, including plants and animals. In contrast, aspartic proteinases seem to be found only in eukaryotic organisms. Since these enzymes are used to break down protein the origin and/or the location of the enzymes determines whether they are beneficial or detrimental to a given organism. For example, where the enzymes are used by pathogens or parasites or pests they are typically used to break down host cell tissue and are therefore detrimental.

Pathogens, parasites or pests such as bacteria, fungi, plants, insects, nematode worms etc produce proteinases which break down host cell tissue to the detriment of the host.

For example, annual global crop losses caused by fungi exceed a thousand million pounds. The pathogen, *Botrytis cinerea* is of major economic importance because it causes disease in thirty crop plant species, with serious losses incurred in the glass house, in viticulture and as a result of post-harvest disease of fruit and vegetables. This major pathogen can be overcome with fungicides but unfortunately, there are disadvantages associated with the use of fungicides in order to control it. These include a financial burden associated with use of the fungicide, the potential environmental hazard arising from the use of toxic fungicides, with attendant consumer concern, and major problems of pathogen resistance to fungicides. In addition, many fungicides are effective against only a limited range of pathogenic fungi.

The above disadvantages are also common to the use of synthetic agents manufactured against other pathogens, parasites or pests such as insects, or specific insects, bacteria or specific bacteria and other eukaryotic organisms including, but not limited to: protozoa such as amoebas, intestinal flagellates and ciliates, haemoflagellates, such as leishmania or trypanosomes, sporozoa, such as those responsible for malaria, arthropod-borne organisms; helminths such as trematodes or flukes, cestoidea, acanthocephala, nematodes, trichuris, trichinella, hook worms, filariae, spiruroids; arthropods such as acarina or mites, ticks heteroptera, lice, fleas, diptera such as disease-carrying flies including mosquitos, maggots and myiasis.

Inhibition of proteinases is known to occur naturally following pathogen infection. For example, it has been shown that following infection by *Phytophthora infestans* varieties of tomato able to resist the fungus show increased levels of proteinase inhibitors (1). This relationship between resistance and the capacity to produce proteinase inhibitors has been used to good effect in the control of pathogen, pests and parasitic diseases. For example, in the most relevant prior art known to the applicant, plant pests are controlled by recombinantly introducing a proteinase inhibitor, animal-derived egg white cystatin, into a selected monocotyledon such as a cereal, forage or turf grass, or a dicotyledon such as a vegetable, tube, or sugar crop, (EP 0 348 348). Similarly, plant nematode pests have been controlled using a proteinase inhibitor, plant-derived cowpea trypsin inhibitor, which has been recombinantly introduced into tobacco, tomato, cotton, oilseed rape, vegetable crop or ornamental plants (EP 0 502 730). In addition, it has been suggested that proteinase inhibitors can be used as anti-parasitic proteins which ideally can be administered to a host species either in a medicament or a food (UK Patent Application No. 94 03819.7).

It is therefore known to use proteinase inhibitors to neutralise the effects of proteinases and so combat the effects of pathogens, parasites or pests. In particular, it is known to transgenically produce plants which are provided with a specific proteinase inhibitor, such as a cysteine proteinase inhibitor.

However, it is the object of the present invention to provide a modified proteinase inhibitor which has greater efficacy than that of its unmodified counterpart or the natural proteinase inhibitor; or alternatively to synthetically manufacture and improve a proteinase inhibitor so as to provide, in one embodiment a hybrid proteinase inhibitor.

In one aspect of our invention we have focused on the group of proteinase inhibitors known as cystatins. The protein sequences of approximately 25 cystatins are known. It is possible to undertake alignment studies of these sequences in order to provide a basis for identifying structural similarities. It has been suggested that there are sufficient differences between plant and animal cystatins to justify separate classification of the two, indeed, a comparison of a plant cystatin, Oryzacystatin I Oc-I [DNA sequence structure shown in FIG. 3, SEQ ID NO:30], and an animal cystatin, egg white cystatin, reveals a significant number of differences showing that overall amino acid conservation is not high. Moreover, there are significant differences in the binding properties of animal and plant cystatins. Thus the dissociation constant Ki varies, for example, egg white cystatin has a Ki of $5\times10^{-12}$M, whereas the plant cystatin, Oc-I, (derived from rice), has a Ki of $3\times10^{-8}$M.

Alignment data of a number of cystatins (SEQ ID NO:1–28) is shown in FIG. 1. The amino acids are numbered 1–181. It can be seen that there is a conserved inhibitory site at alignment amino acids 100–104, represented by the motif QVVAG (SEQ ID NO:56) or QLVAG (SEQ ID NO:57). In addition, it can be seen that there is a conserved PW motif at alignment amino acids 160–161.

This conservation occurs in approximately two thirds of the known sequence structures and is thought from structural studies to be involved in the functioning of the protein and thus for inhibition of proteinases. However, some cystatins with low Ki values do not possess this PW motif therefore its importance in cystatin function is unclear.

Other works have recombinantly manufactured novel cystatins. For example, the human cysteine proteinase inhibitor cystatin C, which participates in the intracellular catabolism of proteins and peptides, in the proteolytic conversion of prohormones, in the extracellular degregation of collagen and in the penetration of normal tissues with malignant cells, has been altered. Workers have modified cystatin C so that one or more amino acids at positions 5–17, 55–59 and/or 68 have been replaced by other amino acids thus retaining the total 120 amino acids in the sequence structure. Modifications were undertaken in order to provide an animal-derived cystatin C considered to have constant activity. (WO 88/09384).

We have found, surprisingly, that site-directed modification of a plant cystatin such as, for example, Oryzacystatin I (Oc-I) can improve its binding properties and thus improve the efficacy of the enzyme in inhibiting proteinases. The site-directed modification involves elimination of the amino acid aspartic acid at position 86 of the amino acid sequence structure of the plant cystatin, this elimination improves the Ki 13 fold, that is to $2.3\times10^{-9}$M. This modification is represented by elimination of aspartic acid (symbol D) at position 163 of the alignment amino acids shown in FIG. 1.

Clearly, this improvement in plant cystatin Ki does not exceed animal cystatin Ki, and particularly egg white cystatin. However, there is growing concern about the liberal approach to cross species transgenics. That is to say the introduction into one species of genes wholly from another species, such as for example, the introduction into plants of human genes encoding human proteins and visa versa. Until our understanding of the consequences of genetic manipulation is complete is would seem prudent to err on the side of caution and thus adopt a more rational approach to genetic manipulation. Thus, plant breeders throughout the world would prefer to combat plant diseases using plant derived proteins, or alternatively, proteins which are significantly similar to plant proteins such that their structural, biochemical and physiological functions are either the same as, or substantially similar to, or consistent with, that of plant proteins. This letter category includes, but is not limited to hybrid molecules.

Further, many animal cystatins with lower Ki's have several disulphide bonds which are not found in plant cystatins so far characterised. Therefore in order to ensure correct protein folding it may be prudent to use at least partially a plant cystatin in plant systems. Thus, our site-directed modification of a plant proteinase inhibitor, and in particular a plant cystatin, and our hybrid proteinase inhibitor when including at least a part of a plant proteinase inhibitor have provided novel improved proteins for preferred, but not exclusive, use in plant systems.

It is of note that there is very little conservation in the alignment amino acid sequences shown in FIG. 1 above alignment amino acid 104 and therefore this makes our observation all the more startling. Previous site-directed modification studies of cystatins were concentrated on the highly conserved QVVAG motif referred to above, but modification of this region was always detrimental (12).

It follows from the foregoing that it is an object of the invention to provide a novel proteinase inhibitor having improved efficacy at least in terms of its binding to a proteinase.

It is also a further object of the invention to provide a novel proteinase inhibitor, ideally having improved efficacy, but also comprising a hybrid molecule which preferably, but not exclusively, comprises a part of a proteinase inhibitor from a first species and a part of proteinase inhibitor from a second species.

It is a further object of the invention to provide products including the whole or a part of the novel protein, or the whole or a part of the DNA encoding same, and also uses for this novel protein and/or DNA.

According to a first aspect of the invention there is therefore provided a proteinase inhibitor modified or manufactured so that it is more effective at inhibiting a proteinase with which it interacts than its corresponding naturally occurring counterpart.

Ideally, said proteinase inhibitor binds more strongly to the proteinase.

Accordingly there is provided a synthetic proteinase inhibitor which has a Ki with at least a 10 times lower value than its natural counterpart. For instance a change in Ki from $3\times10^{-8}$M to at least $3\times10^{9}$M represents such an improvement in Ki.

According to a second aspect of the invention there is provided a proteinase inhibitor including at least one site-directed amino acid deletion and/or substitution which lowers the Ki of the protein at least 10 fold.

Preferably the protein is a cystatin and ideally the site-directed deletion or substitution concerns deletion of either aspartic acid at position 86 of the amino acid sequence structure of Oc-I, or alternatively, deletion of aspartic acid at position 163 of the alignment amino acid sequence structure shown in FIG. 1 of an aligned proteinase inhibitor such as a cystatin, or alternatively, deletion of its functional counterpart in related proteinase inhibitors or cystatins.

Alternatively, the site-directed modification concerns substitution of said aspartic acid at said position for an alternative amino acid which has counter properties having regard to the functional property of the eliminated aspartic acid.

According to a third aspect of the invention there is provided the whole or part of the DNA sequence (SEQ ID NO:29) structure shown in FIG. 2 which DNA sequence structure encodes an example of a protein according to a first aspect of the invention.

All the proteins of the invention, or the corresponding DNA sequence structures have utility in combating diseases whose symptoms are at least partially caused by or characterised by proteinase production. Thus the novel proteins and corresponding DNA sequence structures can be used, directly or indirectly, to prevent, alleviate or mitigate such diseased conditions. For example, a host organism suffering from a pathogenic, pest or parasitic condition involving protein breakdown via proteinases can be treated by receiving at least one protein of the invention. Treatment can be undertaken by applying the said protein of the invention directly to the diseased organism, for example, in the form of a chemical agent such as a pesticide, fungicide etc. or a medicament, or alternatively, by introducing the genetic sequence structure for the said protein of the invention into the genome of the host organism and ensuring that the said inventive protein is expressed by the host organism which organism is then equipped to fight the disease.

In the foregoing paragraph any one or more of the proteins of the invention may be used as aforedescribed. For example, a selected combination of the proteins of the invention, that is to say proteins including site-directed modifications and/or hybrid proteins may be used to counter the effects of any one or more proteinases.

Ideally the transformed organism is a plant.

According to a further aspect of the invention there is provided a method of conferring resistance to proteolytic damage comprising modifying or transforming a host organism so that it expresses the protein of the invention.

According to a yet further aspect of the invention there is provided a construct including a whole or part of the DNA sequence structure of the invention. Said construct may include a plasmid or a vector.

According to a yet further aspect of the invention there is provided use of the protein or DNA sequence structure of the invention as a medicament to combat proteolytic conditions ideally of a pathogenic, parasitic or pest nature.

According to a further aspect of the invention there is provided a composition effective against pathogenic, parasitic or pest diseases including the protein of the invention.

According to a yet further aspect of the invention there is provided a transgenic plant transformed with DNA encoding the protein of the invention, and ideally the DNA shown in FIG. 2, which DNA is coupled to a suitable promoter sequence so that the protein of the invention can be expressed. Ideally, expression is either generally within the plant or in the locale of the pest, pathogen or parasite interaction with the plant. As examples reference 13 provides general methods for identifying promoters from the locale of a pest, pathogen or parasite of a plant. Alternatively, or in addition expression may be selected so as to occur at a selected given point in time.

Preferably said transformed plant is a cereal crop, vegetable crop, oil crop, sugar crop, forage or turf grass, fibre plant, herbalspice plant, fruit crop or indeed any decorative plant.

According to a yet further aspect of the invention there is provided a transformed organism, plant or otherwise, which includes DNA encoding the protein of the invention, and ideally the DNA shown in FIG. 2, so that said protein can be harvested for the purpose of providing sources thereof.

Preferably, said construct is provided with suitable promoters for ensuring expression of the protein of the invention.

According to a yet further aspect of the invention there is provided a method for controlling a pathogen, parasite or pest comprising exposing said pathogen, parasite or pest to the protein of the invention.

According to a further aspect of the invention there is provided use of the protein of the invention to control a pathogen, parasite or pest.

According to a vet further aspect of the invention there is provided any one or more of the primers shown in Table 2, or primers of similar nature having additions, deletions or modifications thereto which still enable the primers to function as described herein.

The modified proteinase inhibitors of the invention may also include novel combinations of proteinase inhibitors either derived from the same or different kingdom, phylum, class, order, family, genus or species. For example, fraction(s) of animal-derived proteinase inhibitor may be combined with fraction(s) of plant-derived proteinase inhibitor, all or one or more of which may or may not include the aforedescribed modification to improve efficacy. Or alternatively, different sorts or types of plant proteinase inhibitors may be combined to provide a novel plant proteinase inhibitor, or alternatively, different sorts or types of animal proteinase inhibitors may be combined to provide a novel proteinase inhibitor, all or one of more of which may or may not include the aforedescribed modification to improve efficacy.

According to a yet further still aspect of the invention there is provided a protein and/or sequence of DNA comprising a first part from a first proteinase inhibitor and at least one other part trom at least one other proteinase inhibitor.

In a preferred embodiment of the invention the DNA sequence of the further still aspect of the invention is provided in a construct so that a corresponding protein can be produced in target tissue such as host cell tissue.

According to a yet further aspect of the invention there is provided target tissue or host cell tissue transformed with the DNA sequence structure of the further still aspect of the invention.

According to a yet further aspect of the invention there is provided a protein comprising a first part from a first cystatin and at least one other part from at least one other cystatin.

In a preferred embodiment said first part of said DNA sequence or said protein comprises plant-derived cystatin DNA or protein respectively, and said at least one other part comprises animal-derived cystatin DNA or protein respectively.

Ideally said animal-derived DNA or protein corresponds to DNA or protein from the active site of animal-derived cystatin; and preferably said plant-derived cystatin DNA or protein corresponds to DNA or protein from a structural site or structural sites or said plant-derived cystatins.

Alternatively, said DNA sequence or protein comprises different sorts or types of plant-derived cystatins.

Alternatively again, said DNA sequence or protein comprises different sorts or types of animal-derived cystatin.

According to a yet further aspect of the invention there is provided protein and/or DNA sequence structure relating to a novel proteinase inhibitor comprising both the aforementioned hybrid proteinase inhibitor and also the aforementioned site-directed modification.

All of the proteinase inhibitors of the invention have application for countering the effects of proteinases and for use in methods relating to such effects.

Thus generally speaking the invention relates to the re-design of proteins which exhibit improved functional activities. Site-directed modifications or regions of amino acid sequence are replaced with either a corresponding region of a protein (from any organism) which exhibits the desired characteristics, or with designed synthetic sequences. The amino acid framework of the original protein is ideally maintained in the final hybrid molecule.

The invention will now be described by way of example only with reference to the following figures wherein:

FIGS. 1A–C show the alignment sequence structure of a number of cystatins.

FIG. 2 shows the DNA sequence (SEQ ID NO:29) structure of the novel protein of the invention.

FIG. 3 shows the DNA sequence structure of the rice cysteine proteinase inhibitor Oryzacystatin Oc-I, (SEQ ID NO:30).

Figure 4A:
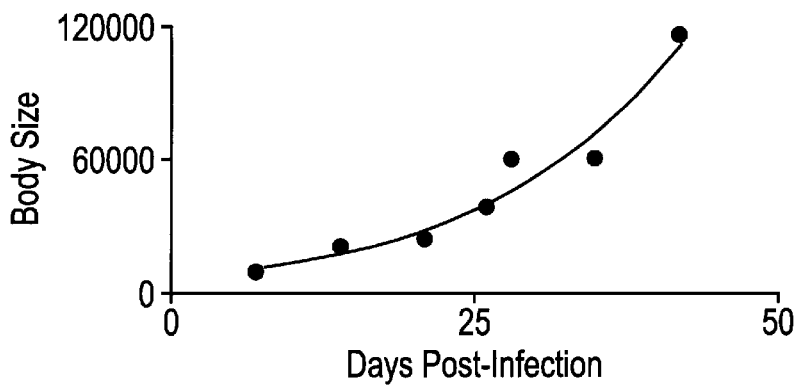
Figure 4B:
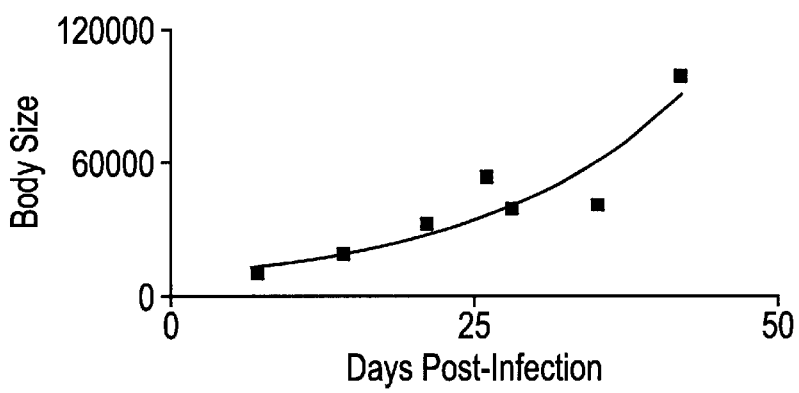
Figure 4C:
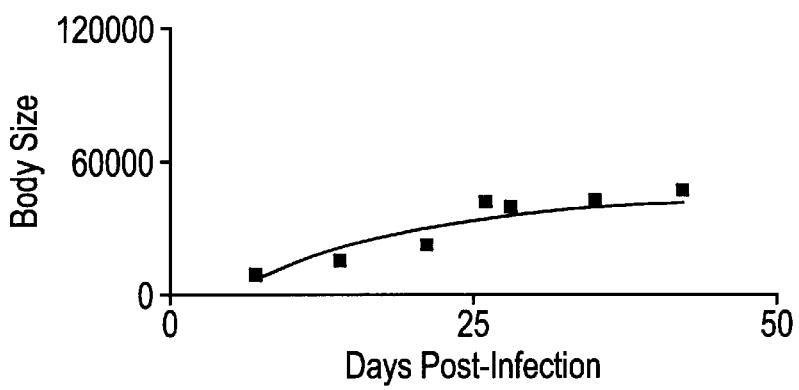

FIGS. 4A–C show the effect of cystatin expression on growth of G.pallida females parasitising A. rhizogenes-transformed tomato roots. Body size of the nematode is given as the area of its outline in sq $\mu$m; (A) controls, (B) and (C), Oc-I and Oc-IdeltaD86 expression respectively.

Figure 5:
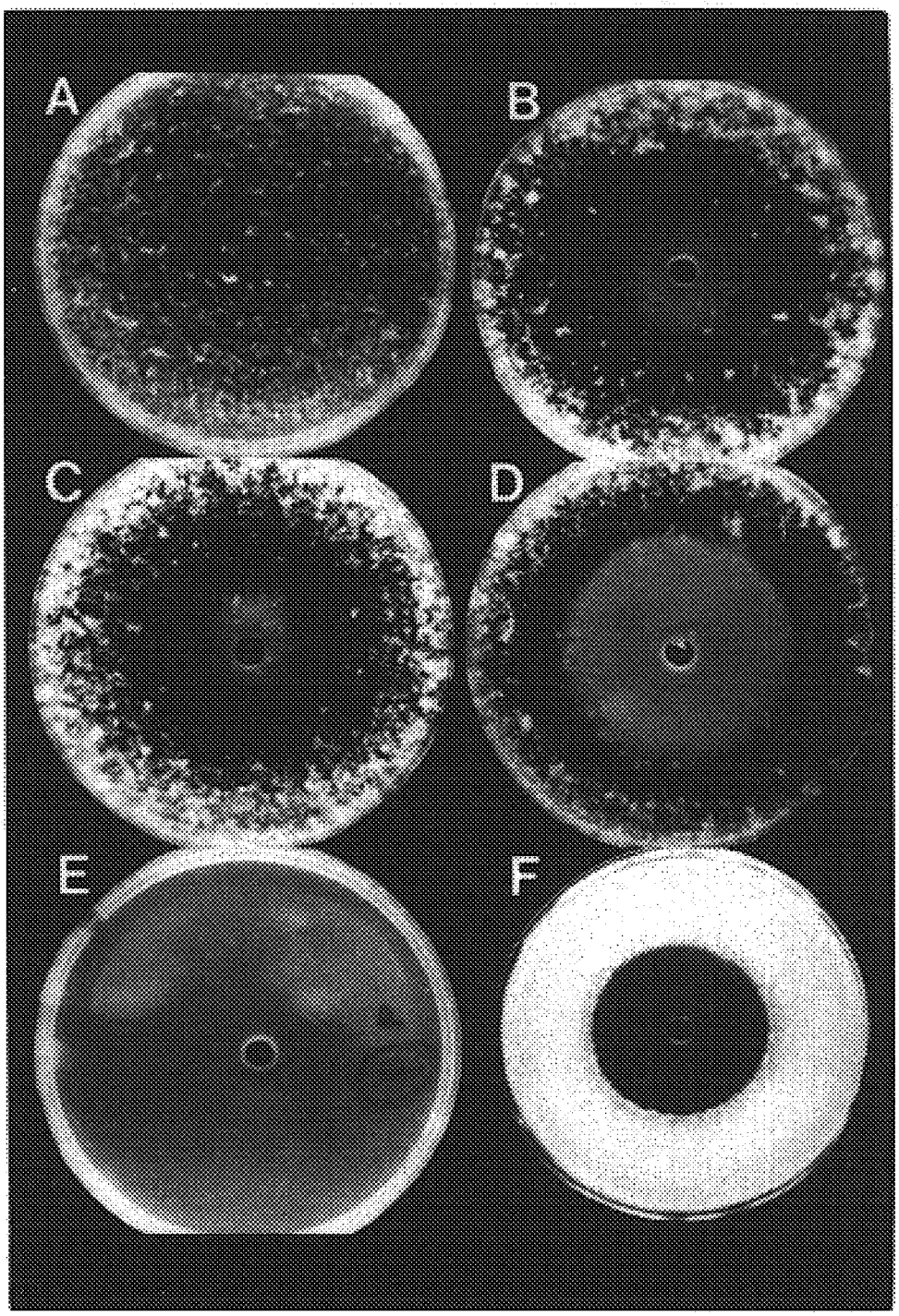

FIG. 5 shows the suppression of growth of fungi from spores over 6 days on agar after addition of a total of 45 $\mu$gPI(s) to the central well (panels A–F).

Figure 6:
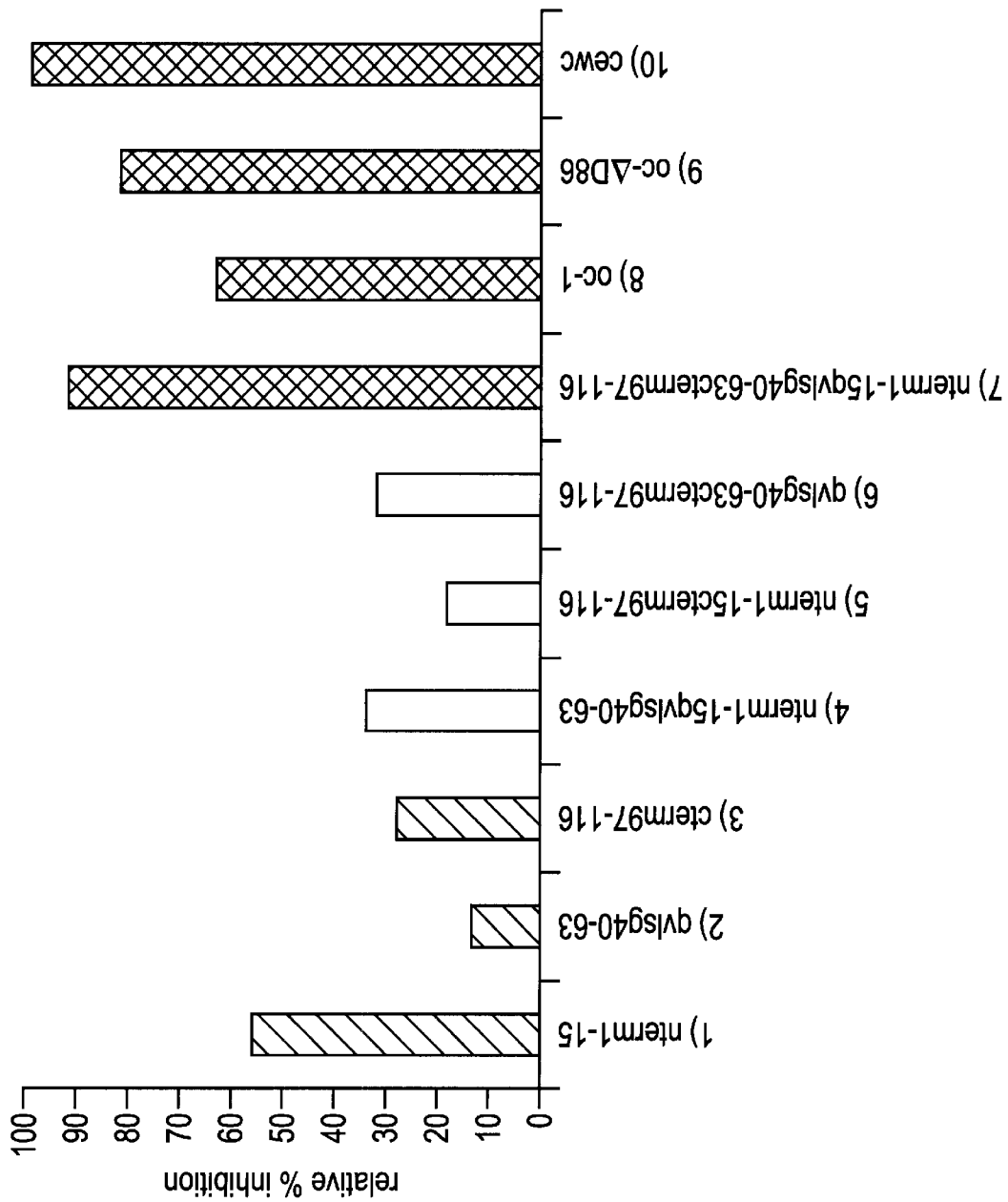

FIG. 6 shows the relative percentage inhibition of various hybrid proteinase inhibitors when exposed to their corresponding proteinases.

Table 1 shows the dissociation constant Ki of a variety of cystatins either in their native state or when subjected to specific modification.

Table 2 shows the sequence of 23 oligonucleotide primers (P1–23) used in PCR reactions and 2 linkers (L1–2) used in cloning, (SEQ ID NO:30–55).

Table 2a shows the sequences of primers (P24–39) used in PCR reactions to manufacture hybrid molecules, (SEQ ID NO:64–79).

Table 3 shows the nature of hybrid molecules manufactured. The bars indicate the length of Oc-I protein, areas shaded black represent the regions replaced by CEWC amino acid sequence.

MATERIALS AND METHODS

Strains and Vectors

DNA Preparation and Manipulation

Plasmid DNA was purified from E-coli cultures by the alkaline lysis method (2). Restriction digests and ligation reactions were carried out using the recommendations of the manufacturer. DNA fragments were recovered from agarose gels using an electroelution chamber (IBI) following the manufacturer's protocol. Oligonucleotides were synthesised on an Applied Biosystems 381 A instrument and further purification was only performed for oligonucleotides used in "Altered Sites II" site directed mutagenesis prbtocols by using a reverse phase COP chromatography cartridge (Cruachem. Glasgow, UK). DNA sequencing of double stranded plasmid DNA was performed using Sequenase version 2.0 (Amersham) according to the manufacturer's instructions.

Cloning of Cystatins and *C. elegans* Proteinase Inhibitor

Oc-I was amplified from genomic DNA of *Orvza sativa L. japanica* with primers P1 and P2 (see Table 2) designed from published sequence data (3) and with the addition of restriction enzyme sites to assist cloning. The intron was removed by the PCR technique of gene SOEing (4a & 4b) where primer pairs P1/P3 and P2/P4 were used to amplify the two exons. These products were then SOEn together by amplifying with primers P1 and P4 and the product cloned into Sma I/Eco R1 digested pBluescript. The sequence of the cloned coding region was verified by comparing with the published data for Oc-I (3). Amplification and intron removal of the *C. elegans* cysteine protease gene, gcp-I, were performed in a similar manner using primers P5–8 (Table 2) designed from sequence information (5). The final PCR product was cloned into pBluescript and checked by sequence analysis.

DNA sequence information for cowpea cysteine protease inhibitor, CCP1 (6) was used to design oligonucleotide primers, P9 and P10 (Table 2). These primers together with a cDNA clone carrying the CCP1 gene (kindly provided by Prof. P. Shewry) were used to PCR amplify a product that was cloned directly into the expression vector pQE30 (Qiagen, California, USA) utilising the Bam HI and Hind III sites incorporated into the PCR primers. Genes were cloned into the Type IV pQE expression vectors (Qiagen, California, USA) (Bam HI/Hind III) and proteins were expressed in the *E-coli* strain M15[pREP4].

Mutagenesis
a) N-terminal Deletions

To generate the large 72 bp deletion at the 5'-end of Oc-I, designated pdelta24Oc-I, pQE30/Oc-I was digested with Sma I and Hinc II, the large fragment purified from an agarose gel and relegated. To create the 63 bp deletion (termed pdelta21Oc-I), pQE30/Oc-I was restricted with Bam HI and Hinc II and gel purified. The 9 bp region irnnediately 5' to the Hinc II site together with the sequence encoding the enterokinase recognition site was reintroduced by ligating the annealed oligonucleotide linkers L1 and L2 to the purified fragment.
b) C-terminal Deletions Exonuclease III/mung bean nuclease deletions were carried out (2) to generate deletions to 24, 27, 30 and 33 bp at the 3'-end of the gene.
c) Point Mutations The "Unique Site Elimination" (USE) strategy (Pharmacia, Upsalla Sweden) was used to generate constructs expressing single codon alternations using primers P11–P20 (Table 2) which resulted in variant forms of Oc-I having the following amino acid alterations. i) insertion of Leu between 81 and 82. ii) deletion of E13; D86; A74; M85; iii) substitution of (from, No, to) D86N; E89L; Q91L; P83A; W84A. "Altered Sites II" system (Promega, Madison, USA) which involved subcloning Oc-I into the vector pALT-Ex2, (Promega, Madison, USA) was used to generate mutants in which the codons for P83, W84 and D86 were changed to the Amber stop codon (TAG). The oligonucleotides (P21–P23) used to achieve this as shown in Table 2 where the amber stop codons are shown in bold and the point mutation to remove a Sac I site (GAGCTC) is in lower case (this change does not alter the amino acid sequence). The absence of this Sac I site was used as a diagnostic test for mutants. The "Interchange" method (Promega, Madison, USA) was to used to generate amino acid changes, to Cys, Glu, Phe, Gly, His, Pro, Arg, Lys, Gln, Ser and Tyr, at the Amber stop codon by introducing the mutant clones into twelve specific amber suppressing strains.

Expression of Oc-I and gcp-I in *E coli*

Oc-I expressed from pQE30 ("QlAexpression" system) contained six N-terminal histidine residues, encoded by the vector to allow one-step Nickel chelate affinity. Oc-I protein was purified from 1l cultures of *E coli* M15 [pREP4] harbouring the pQE30 derived expression plasmid: 20 ml of an overnight culture was inoculated into 1 litre of LB-media and grown at 37° C. to $A_{600}$ 0.7–0.9. IPTG was added to a final concentration of 2 mM and growth was allowed to continue for a further 2 h. The cells were harvested by centrifugation at 10000 g for 10 min, resuspended in 12 ml of sonication buffer (50 mM $Na_2HPO_4$, 300 mM NaCI) and stored at −20° C. overnight. The sample was thawed, aliquoted to three 15 ml tubes and sonicated on ice in short pulses (3×30 sec). Cell debris was pelleted by centrifugation (10000 g) and approximately 0.5–0.75 ml of Ni-NTA resin slurry (Qiagen, Calif., USA) was added to each tube and mixed gently on ice for 1 h. The resin was collected (1000 g for 1 min) and washed five times with Sml of wash buffer (50 mM $Na_2HPO_4$pH 6.0, 500 mM NaCI, 40 mM imidazole at 4° C. for 0.5 h). Protein was eluted with lml of elution buffer (50 mM $Na_2HPO_4$, 300 mM NaCI, 100 mM EDTA) and the resin was repelleted at 1000 g for 1 min and the elution repeated a further two times.

The *C. elegans* proteinase glp-1 was expressed in an identical manner.

Delta2IOc-I contained an enterokinase recognition sequence (Asp-Asp-Asp-Asp-Lys, SEQ ID NO:58) between the N-terminal six histidines (6×His-tail) and the N-terminal residue of the truncated Oc-I protein. Enterokinase (Boeringer) was used to cleave the 6x His-tail from Delta21Oc-I, which was purified from the 6×His-tail by nickel affinity chromatography. "Centricon 10s" (Amicon) were used according to instructions provided with the product to separate Oc-I from contaminating enterokinase.

Determination of Ki's

To determine the Ki of cystatins biochemical assays were performed according to the procedure of Barrett (7) and Ki values were calculated as described by Abe et al. (3)

SDS PAGE and Western Blot Analysis

All purified proteins were analysed by SDS-PAGE (8). Westem blots were performed according to the protocol for "mini protein II" (Biorad, Hertfordshire, UK) using PVDF membrane (Millipore, Massachusetts, USA).

Antibody Production

Polyclonal antibodies against Oc-I were raised in male Wistar rats (6 weeks old). Three interperitoneal injections of 100 ug Oc-I in a final volume of 300 ml were given at four week intervals. The first injection was an emulsion of protein and complete Freunds adjuvant in a 1:1 (v/v) ratio and the second and third injection were similar but used incomplete Freunds adjuvant. Ten days after the final injection, blood was collected and allowed to coagulate at 4° C. before centrifugation at 5000 g for 10 min. The resultant serum was collected and stored in 50% (v/v) glycerol at −70° C. The serum gave optimal results in ELISA at a dilution of 1 in 10000 and recognised both native and denatured Oc-I protein.

ELISAs

ELISAs were performed to determine the level of expression of cystatins in transgenic roots. Root segments of about 2mm were ground in liquid nitrogen, transferred to a 15 ml Falcon tube prior to the addition of 1 ml of 0.5×PBS was added and shaking at 4° C. for 15 min to dissolve the soluble protein fraction. Protein was acetone precipitated and the precipitant was resuspended in coating buffer (15 mM $Na_2HCO_3$, 34 mM $NaHCO_3$, pH 9.6). Protein concentration was determined by a standard assay (14). Wells of a Maxisorb microtitre plate were coated with 100 mg protein for 48 h at 4° C. Plates were blocked with anti-Oc-I antibody (1 in 10,000 dilution). Activity was detected by adding substrate and the absorbance of the samples was measured at 405 nm when coloration developed.

Different amounts of Oc-I were added to aliquots of 100 mg of total protein extracted from untransformed roots and used concurrently in ELISA. assays with unknown samples to provide internal standards over the range of 0–2% Oc-I in total soluble protein.

Culture of *Celegans*

Caenorhaboditis elegans was cultured on NGM agar carrying a lawn of *E-coli* OP50 cells as described by Wood (9). Populations were maintained for 5 days before an agar plug was inserted into fresh media. When required, cystatins were added to the media at a final concentration of 2.5 mg $l^{-1}$ just prior to polymerisation. Single nematodes were transferred from non-supplemented solid agar plates to plates containing Oc-I, DeltaD86 Oc-I or BSA. Where necessary ten replicates were carried out for each treatment.

Transgenic Tomato Root Culture

Oc-I derivative genes were cloned into the vector pBIN19 and then introduced into *Agrobacterium rhizogenes* strain LBA9402 by electrotransformation for use in transformation of *Lycopersicon esculentum* cv Ailsa Craig by a standard protocol (15). Subsequently roots were grown on 0.5× Murashige and Skoog basal salts mixture supplemented with Gamborgs B5 vitamins and 3% sucrose (w/v) and 0.2% phytagel (w/v) plus 100 mg $l^{-1}$ kanamycin, solid medium, during initial selection. Western blots were used to confirm the presence of Oc-I or mutant forms in putatively transformed roots.

Challenge of Roots by *Globodera pallida*

The J2 were obtained from cysts of *G.pallida* and sterilised extensively before use. The cysts were soaked in running tap water for 2–3 days followed by an overnight soak in 0.1% (v/v) malachite green at room temperature. Cysts were then rinsed for 8h in running tap water prior to soaking overnight at 4° C. in an antibiotic cocktail (8 mg $ml^{-1}$ streptomycin sulphate, 6 mg $ml^{-1}$ penicillin G, 6.13 mg $ml^{-1}$ polymycin B, 5mg $ml^{-1}$ tetracycline and 1 mg $ml^{-1}$ amphotericin B). The cysts were then washed in filter-sterilised tap water and set to hatch in filter-sterilised potato root diffusate. The overnight hatch of J2s was counted and sterilised sequentially for 10 min with the following antibiotics; 0.1% streptomycin sulphate, 0.1% penicillin G, 0.1% amphotericin B and 0.1% cetyltrimethylammoniumbromide (Cetavlon). The nematodes were pelleted between treatments by, brief microcentrifugation. They were washed extensively in filter sterilised tap water and used immediately. Roots of transformed lines were cultured for 4 weeks before 2 cm lengths were transferred to fresh media. After a further 3–4 days, 5ml aliquots containing 35 J2s were pipetted onto each actively growing root approximately 1 cm from its tip. A 1 $cm^2$ piece of sterile GFA filter paper was placed over the area to aid infection and was removed 24 h later.

At harvest infected roots were removed from petri dishes, rinsed in water and placed in 1% (w/v) sodium hypochlorite for 2 min. For early time points, roots were plunged into boiling 0.1% aqueous acid fuchsin for 1 min, rinsed in water and then cleared in acidified glycerol at 60° C. overnight to facilitate visualisation of nematodes. At the later time points, nematodes could be visualised without staining and were dissected from the roots. Nematodes were examined under a microscope (DBRM, Leica) at 50–200×magnification and the cross-sectional area was measured using an image analyser (Quantimet 5000° C.; Leica) attached to the microscope.

Demonstration of Antifungal Activity

We have shown that the PIs recovered after expression in pQE30 (see earlier) have anti-fungal activity. 45 µg of the recovered P1 were added at 1 µg/µl to a central well within agar plates which contained spores of *B. cinerea* ($2.2 \times 10^4$/plate). The spores do not germinate and the fungus failed to grow where CPTI or Oc-I has diffused into the agar from the central well. The potent effect persisted for many weeks and was enhanced by combining a serine and cysteine PI. Of particular relevance is that Oc-IdeltaD86 was more efficacious than the native form of Oc-I(FIG. 3). We have also established that PIs have effects on other micro-organisms including *Aspergillus fumigatus* (a fungal pathogen of mammals; FIG. 5) and *Erwinia carorovora* (a bacterial pathogen of plants). This demonstrates two of the central points underpinning this application viz. (i)the approach has a broad potential against very different fungi (ii) protein engineering can enhance the efficacy of PIs against fungi.

Formation of Hybrid Genes

Chicken egg white cystain (CEWC) is a more potent inhibitor than either Oc-I or Oc-IΔD86. We have replaced fragments of Oc-I with the corresponding sequences of CEWC in order to create a gene of essentially plant origin with the more potent inhibitory properties.

Materials and Methods

Replacement of the N-terminus of oc-I With the Corresponding Region of cewc.

Two oligonucleotide primers (P24 and P25) were synthesised which were overlapping at their 3' ends. These were annealed and filled-in with DNA polymerase I (Klenow fragment) to generate a double-stranded full-length sequence encoding the N-termninus of the mature form of CEWC, S E D R S R L L G A P V P V D (SEQ ID NO:59, residues 1–15, CEWC numbering). Primers P26 and P27 were used to amplify oc-I lacking the first 51 bp of coding sequence. The oc-I and cewc sequences were then joined by a PCR reaction known as SOEing (4a & 4b) to generate hybrid gene termed oc-nterm 1–15.

Replacement of the Central QVVAG and Surrounding Region of oc-I With the Corresponding Region of cewc.

A second hybrid molecule was constructed in which the central loop of the tripartite wedge, which comprises the active site of Oc-I, was replaced with the corresponding portion of CEWC. Four oligonucleotides (P28, P29, P30 and P31) were synthesised which when together encoded the CEWC sequence Y S S R V V R V I S A K R Q L V S G I K Y I L Q (SEQ ID NO:60, residues 40–63). Primer pairs P28/P29 and P30/P31 were annealed and treated with DNA polymerase I (Klenow fragment) to generate two double-stranded fragments which were subsequently SOEn together. Fragments of oc-I encoding both the N- and C-terminal regions were amplified using primers P32/P33 and P27/P34 respectively. The synthetic cewc sequence (P28–31) was SOEn to the N-terminal fragment of oc-I which was in turn SOE-n to the C-terrninal fragment of oc-I generating the hybrid gene glvsg40–63.

Replacement of the C-terminus of oc-i With the Corresponding Region of cewc.

The region of cewc encoding the C-terminal 20 amino acids, F V V Y S I P W L N Q I K L L E S K C Q (SEQ ID NO:61, residues 97–116) was generated, using primers P35 and P36 in an identical manner to that encoding the N-terminus described above. Primers P32 and P37 were used to amplify oc-I lacking the terminal 51 bp of coding sequence. The oc-I and cewc sequences were SOEn together to generate the hybrid termed oc-cterm97–116.

Generating Hybrids With Shorter cewc Sequences

To determine whether shorter cewc regions could confer greater inhibitory potency than native Oc-I in a hybrid cystatin further hybrid molecules containing smaller regions of CEWC were generated. Such hybrid proteins would retain more of the amino acid sequence of the original plant molecule. Two primers P38 and P39, where used in USE mutagenic reactions, this generated two hybrid genes terms oc-qlvsg52–60 and oc-pw101–107 which encoded the contiguous cewc residues R Q L V S G I K Y (SEQ ID NO:62, residues 52–60 critical cewc active site [12]) and S I P W L N Q (SEQ ID NO:63, residues 101–107, important region of C-terminus [16]) respectively.

Generating a Matrix of Hybrid Molecules

Hybrid molecules in which multiple sections of oc-I have been replaced by the corresponding cewc sequences were generated by utilising conveniently situated restriction enzyme sites in oc-I. Sequences encoding the N-terminus of either the native oc-I or the N-terminal hybrid gene were removed by Hinc II restriction digest. Sequences encoding the C-terminus of either native oc-I of the C-terminal hybrid gene were removed by Foc I-restriction digest. By ligating a fragment from one hybrid gene to that of another, further hybrid molecules were generated in which two or three of the original oc-I fragments were replaced by those of cewc. A total of 15 hybrid genes were constructed (Table 3).

RESULTS

Modelling

Protein sequence alignments were generated using the program SOMAP to align protein sequence selected from the OWL database. An initial alignment of cysteine proteinase sequences served to demonstrate the high degree of conservation throughout the cysteine proteinase family and also confirmed that using papain as our initial target was not unreasonable. A second aligned twenty five cysteine proteinase inhibitors (FIG. 1) of available sequences was generated and served to highlight previously identified conserved amino acids and provided a basis for comparing known Ki values of cysteine protease inhibitors with sequence features, information which was used in the design of mutagenesis strategies.

For structural modelling the co-ordinates of hen egg white cystatin (10) and human stefin B/papain complex (11) were kindly provided by Prof. Bode. These were used to build a three dimensional model of OcI which was then energy minimised using the program Xplor to ensure that our model had reasonable stereochemistry.

Cloning Expression and Purification of *C. elegans* Cysteine Protease

In order to allow Ki values to be determined against both papain and a nematode protease the *C. elegans* cysteine proteinase was expressed and purified from *E coli* gcp-1 preparations and analysed by SDS PAGE to determine purity.

Expression and Mutagenesis of Cystatins

Cystatins and Oc-I mutational variant proteins expressed and purified from *E coli* were analysed by SDS PAGE to determine the level of purity.

The alignment of the cysteine proteinase inhibitors (FIG. 1) shows that Oryzacystatins have no leader sequence (unlike the maize homologues) and are therefore likely to be produced intracellularly. For the three wild type inhibitors, Cowpea protease inhibitor (CCPI), maize cystatin II and Oc-I determination of Ki demonstrated that they have similar inhibitory activities. At the onset of the work CCP1 was not characterised. For these reasons Oc-I was selected for mutational analysis.

Previously published reports suggested an N-terminally truncated form of Oc-I was marginallv more efficacious than the-native protein-however, although these variant Oc-I proteins lacked 21 and 24 amino acids of Oc-I they retain N-terminal sequences encoded by vector sequences which might therefore have contributed to interactions with the proteinase. To examine this question proteins were expressed with N-terminal 24 and 21 amino acid deletions and C-termninal 8, 9, 10, 11 and 12 amino acid deletions. The Ki of these variant protein forms were determined using either papain or *C. elegans* protease, gcp-1 (Table 1). None of the truncated proteins were found to have a lower Ki than wild type Oc-I and both 21 and 24 amino acid deletions were inactive, suggesting that the results of other workers were due to the additional vector residues contributing to activity.

Protein sequence alignments and the model of Oc-I together with published Ki values for cystatins were used to identify mutations that might improve the inhibitory capability of Oc-I. The amino acid E13 and D86 were deleted independently. The deletion of residue E13 had no effect on the Ki Oc-I against either papain or gcp-1. Deletion of residue Delta86 lowered the Ki of Oc-I approximately 13-fold from 7 nM to 0.5 nm with papain and 8 nM to 0.6 nM with the *C. elegans* protease, gcp-1 (Table 1). The region of the inhibitor around D86 was targeted for further mutagenesis. Table 1 shows Ki values for all the further mutations assayed against the *C. elegans* cysteine protease.

It is apparent from these figures that all of the substitutional mutations led to an increased Ki suggesting a decreased efficacy. The only mutation which showed a similar or marginally decreased Ki value to that of wild type Oc-I was the deletion of residue M85 (from 8 to 7.1 nM with gcp-1).

In vivo Effect of Cystatins Against *C. elegans*

Feeding trials were set up using *C. elegans* to examine the effect of protease inhibitors on nematode growth. As soon as hermophrodites became apparent on normal agar they were transferred to individual plates containing either Oc-I, Oc-IdeltaD86, CCPI or BSA and egg laying was observed. Irrespective of the culture media the hermaphrodites laid a mean number of approximately 300 eggs. Half of these eggs were removed to normal plates containing no added inhibitor. The eggs were allowed to hatch and the development of the *C. elegans* larvae was monitored. Under all conditions greater than 95% of the eggs hatched and development was completed for 94%, 92.5%, 97% and 96% of those hatched from eggs recovered from Oc-I, Oc-IdeltaD86, CCPI and BSA supplemented media respectively.

In a second experiment larvae hatching under normal conditions were removed to media supplemented with a protein as above. 50 larvae were transferred at 6 h, 12 h, 24 h and 30 h corresponding to the developmental times when the four larval stages L1, L2, L3 and L4 predominate. No larvae developed to an adult when transferred to media supplemented with Oc-I, Oc-IdeltaD86 or CCP1 at 6, 12 or 24 h after hatching. The larvae which failed to develop on cystatin supplemented media became moribund and failed to recover on transfer to fresh non-supplemented plates. These larvae also failed to move or respond to repeated tactile stimuli and eventually died. However 76% of larvae transferred at 30 h after hatching developed to reach the adult male or hermaphrodite stages. All juveniles hatched from eggs laid on media containing BSA and transferred to normal media developed into adult nematodes.

In Vivo Effect of Cystatin Against *Globodera pallida*

Preliminary assays with Oc-I and Oc-IdeltaD86 demonstrated that anti-Oc-I polyclonal antibodies both recognised both proteins equally well. ELISA established that the highest level of expression in an Oc-I expressing transformed tomato hair root line was 0.54+0.02% of the total soluble protein. Similar assays identified a Oc-IdeltaD86 line with a similar level of expression of 0.51+0.01% of the total soluble protein fraction which was selected for comparative studies. The growth of nematodes on the two transgenic cystatin lines and an untransformed control was measured for individuals recovered from several roots at approximately weekly intervals for 6 weeks. Image analysis provided values for the area of the nematode outline. Means for these values are given against time for three root lines in FIG. 4. Statistical analysis was carried out using oneway ANOVA with an a priori contrast (12) to compare the two cystatin lines against the control for each day of measurement. This analysis establishes a significantly lower outline area (P<0.05) at 1, 2, 4, 5 and 6 weeks. Furthermore no significant increase in size occurred between 4 and 6 weeks for animals on Oc-IdeltaD86 line (P<0.05;SNK) in contrast to the other two lines. Comparative assays as described by Urwin et al (16) in which inhibition by CEWC was determined arbitrarily as 100%, have been carried out the first seven hybrid molecules listed in Table 3. Of those seven only one, OC-NTERM1–15QVLSG40–63CTERM97–116, which contains 57 CEWC residues displayed inhibition of c.a. 90%. This was greater than native Oc-I (c.a. 60%) and Oc-IΔD86 (c.a. 88%). The level of inhibition observed for the remaining six hybrid molecules was reduced (FIG. 6).

Discussion

It can be seen from the data shown in Table 1 that removal of the aspartic acid at amino acid position 86 improved the Ki value some 13–14 fold whilst deleting methionine at neighbouring position 85 had only a marginal effect on papain inhibition. Additionally, substitution of aspartic acid at position 86 by 12 other amino acids had a detrimental effect on Ki. Therefore, removal of one amino acid, thus shortening the protein backbone, seems to be a significant factor in improving Ki. Moreover, the removal of an amino acid at position 86 seems to be important. We consider that the loop containing this residue is part of the inhibitory site of the molecule with deletion of amino acid aspartic acid 86 resulting in a more similar structure to that of other cystatins perhaps improving the interaction of the conserved above referred to PW site at amino acid positions 83 and 84 with the proteinase.

In Table 1 it can be seen that the efficacy of the native and modified proteinase inhibitors was determined having regard to papain and also gcp-1 derived from the bacteria-feeding nematode *C. elegans*.

Moreover, other information presented herein shows that the modified protein is effective at inhibiting proteinases and so functionally active.

In addition, our data relating to hybrid molecules shows that it is possible to engineer proteins and in particular to modify plant proteins to include at least a part of an animal protein so that the functional effectiveness of a proteinase inhibitor is improved, that is to say the functional effectiveness of a plant protein approaches that of an animal protein.

Our data indicates that previous reports of inadequate control of insects at achievable levels of expression of native proteinase inhibitors may be overcome by using protein engineering as demonstrated in the present application. We have shown that protein engineering can lower and so improve Ki values and so reduce the minimum effective protein level that must be expressed in plants for effective plant protection.

REFERENCES

1) Peng, J H & Black L L (1976) Phytopatholgy. 66:958–963.
2) Maniatis T., Fritsch E F & Sambrook J (eds)(1982). Molecular cloning a laboratory manual. Cold Spring Harbor Laboratory. pp545
3) Abe K, Emori Y, Kondo H, Suzuki K & Arai S. (1987). Molecular cloning of a cysteine proteinase inhibitor of rice (Orozacystatin) Homology with animal cystains and transient expression of the ripening process of rice seeds. *The Journal of Biological Chemistr.* 262: 16793–16797.
4a) Ho S N, Hunt H D, Horton R M, Pullen J K and Pease L R (1989). *Gene* 77: 51.
4b) Horton R M, Hunt H D, Ho S N, Pullen J K and Pease L R (1989). *Gene* 77: 61.
5) Rav C and McKerrow J H (1992). Gut-specific and developmental expression of a *Caenorhabditis elegans* cysteine protease gene. Molecular and Biochemical Parasitology. 51: 239–250.
6) Fernandes K V S, Sabelli P A, Barratt D H P, Richardson M, Xavier-Filho J and Shewry P R (1993). The resistance of cowpea seeds to bruchid beetles is not related to levels of cysteine proteinase inhibitors. *Plant Molecular Biology* 23: 215–219.

7) Barrett A J (1972). A new assay for Cathepsin B1 and other thiol proteinases. *Analytical Biochemistry* 47: 280–293.
8) Hames B D and Rickwood D(eds)(1981). Gel electrophoresis of proteins a practical approach. IRL press limited pp290.
9) Wood B (ed)(1988). The nematode *C. elegans*. Cold Spring Harbor Laboratory press. pp606.
10) Bode W, Engh R, Musil D, Thiele U, Huber R, Karshikov A, Brzin J, Kos J and Turk V (1988). The 2.0 Å X-ray crystal structure of chicken egg white cystatin and possible mode of interaction with cysteine proteinases. *The EMBO Journal* 7: 2593–2599.
11) Stubbs M, Laber B, Bode W, Huber R, Jerala R, Lenarcic B (1990). The refined 2.4 Å X-ray crystal structure of combinant human stefin B in complex with the cysteine proteinase papain: a novel type of proteinase inhibitor interaction. *The EMBO Journal* 9: 1939–1947.
12) Arai S, Watanabe H. Kondo, Emori Y and Abe K (1991). Papain-inhibitory activity of oryzacystatin, a rice seed cysteine protease inhibitor, depends on the central Gln-Val-Val-Ala-Gly region conserved among cystatin superfamily members. *J Biochem*. 109:294–298.
13) Sijmons P C, Atkinson H J and Wyss U (1994). Parasitic Strategies of Root Nematodes and Associated Host Cell Responses. *Annual Review of Phytopathology* 32:235–259.
14) Bradford M, (1976). A rapid and sensitive method for the quantitation of microgramme quantities of protein utilising the principle of protein dye binding. *Analytical Biochemistry* 72:248–254.
15) Tefer D (1984). Transformation of several species of higher plant by *Agrobacterium rhizogenes*. Sexual transmition of the transformed genotype and phenotype. *Cell* 37:959–967.
16) Urwin P E, Atkinson, H J, Waller D and McPherson M J (1995). Engineered Oryzacystatin-I expressed in transgenic hairy roots confers resistance to *Globodera pallida*. The Plant Journal 8: 121–131.

What is claimed is:

1. A modified cystatin with greater efficacy in inhibiting proteinase than its unmodified counterpart, said modified cystatin comprises at least one site-directed amino acid deletion, wherein the deletion is of aspartic acid at position 86 of oryzacystatin 1.

2. A composition comprising the proteinase inhibitor of claim 1.

3. The composition of claim 2, which further includes a suitable carrier.

4. An isolated DNA molecule encoding the proteinase inhibitor of claim 1.

5. A DNA construct comprising the isolated DNA molecule of claim 4.

6. A host cell transformed with the DNA construct of claim 5.

7. The host cell of claim 6 which is a plant cell.

8. A method of conferring resistance to proteolytic damage on a host cell, said method comprising transforming the host cell with the DNA construct of claim 5, wherein the transformed host cell expressing said DNA molecule is rendered resistant to proteolytic damage.

9. The method of claim 8, wherein the DNA molecule is expressed under the control of a selected promoter, so that the modified cystatin is either expressed at a given selected point in time or at a given location in the host cell.

10. The method of claim 8 or 9, wherein said host cell is a plant cell.

11. The method of claim 10, wherein said plant cell is from a cereal crop.

12. A method of producing a proteinase inhibitor, wherein the proteinase inhibitor is the modified cystatin of claim 1, the method comprising: transforming a host cell with a DNA molecule encoding said cystatin, modified culturing the transformed host cell under conditions wherein said proteinase inhibitor is expressed, and harvesting the expressed proteinase inhibitor.

13. A method for controlling a pathogen or pest, comprising exposing said pathogen or pest to the modified cystatin of claim 1.

14. A method for countering the effects of a susceptible proteinase, comprising contacting said proteinase with the modified cystatin of claim 1.

15. The method of claim 13, wherein the modified cystatin provides pesticide activity.

\* \* \* \* \*